US012345718B2

(12) United States Patent
Cambot et al.

(10) Patent No.: US 12,345,718 B2
(45) Date of Patent: Jul. 1, 2025

(54) METHOD FOR DETERMINING THE HAEMOGLOBIN CONTENT OF AN ERYTHROID CELL

(71) Applicants: UNIVERSITÉ PARIS EST CRÉTEIL VAL DE MARNE, Créteil (FR); Assistance Publique—Hôpitaux de Paris, Paris (FR); ÉTABLISSEMENT FRANÇAIS DU SANG, Saint-Denis (FR); Institut National de la Santé et de la Recherche Médicale, Paris (FR)

(72) Inventors: Marie Cambot, L'Haÿ-les-Roses (FR); Gaetana Vandemeulebrouck, Paris (FR); France Noizat Pirenne, Paris (FR); Pablo Bartolucci, L'Haÿ-les-Roses (FR); Marie Georgine Rakotoson, Antananarivo (MG); Frédéric Galacteros, Santeny (FR); Nicolas Hebert, Ollainville (FR)

(73) Assignees: UNIVERSITÉ PARIS EST CRÉTEIL VAL DE MARNE, Creteil (FR); ASSISTANCE PUBLIQUE - HÔPITAUX DE PARIS, Paris (FR); ÉTABLISSEMENT FRANAIS DU SANG, La Plaine Saint Denis (FR); INSTITUT NATIONAL DE LA SANTÉ ET DE LA RECHERCHE MÉDICALE, Paris (FR)

( * ) Notice: Subject to any disclaimer, the term of this patent is extended or adjusted under 35 U.S.C. 154(b) by 932 days.

(21) Appl. No.: 17/395,969

(22) Filed: Aug. 6, 2021

(65) Prior Publication Data
US 2022/0011324 A1    Jan. 13, 2022

Related U.S. Application Data

(63) Continuation-in-part of application No. 16/347,738, filed as application No. PCT/FR2017/053015 on Nov. 3, 2017, now Pat. No. 11,231,427.

(30) Foreign Application Priority Data

Nov. 4, 2016   (FR) ..................................... 1660713

(51) Int. Cl.
G01N 33/72      (2006.01)
G01N 21/64      (2006.01)
G01N 33/49      (2006.01)

(52) U.S. Cl.
CPC ......... G01N 33/721 (2013.01); G01N 33/723 (2013.01); G01N 2333/805 (2013.01); G01N 2800/22 (2013.01); G01N 2800/52 (2013.01)

(58) Field of Classification Search
CPC ....... G01N 15/1459; G01N 2015/0065; G01N 2015/0073; G01N 2015/1006; G01N 2800/22; G01N 2800/52; G01N 33/72; G01N 33/721; G01N 33/80; G01N 33/49; G01N 33/4915; G01N 33/723; G01N 21/6428; G01N 21/6486; G01N 2333/805
USPC ..... 436/63, 66, 164, 172, 536; 435/7.1, 7.25
See application file for complete search history.

(56) References Cited

U.S. PATENT DOCUMENTS

| | | | |
|---|---|---|---|
| 7,485,433 B2 | 2/2009 | Van Weeghel et al. | |
| 7,541,190 B2 | 6/2009 | Van Agthoven et al. | |
| 11,231,427 B2 * | 1/2022 | Cambot | G01N 15/1459 |
| 2004/0214243 A1 * | 10/2004 | Burshteyn | G01N 33/721 436/520 |
| 2011/0117670 A1 * | 5/2011 | Walker | G01N 33/723 530/387.9 |
| 2012/0052516 A1 * | 3/2012 | Baudin-Creuza | G01N 33/721 435/7.1 |

FOREIGN PATENT DOCUMENTS

WO    WO 2003021275 A1    3/2003

OTHER PUBLICATIONS

Amoyal, I. et al., "Hemoglobin switch in the newborn: a flow cytometry analysis.", Neonatology, 91: pp. 61-68 DOI: 10.1159/000095973 (2007).

Amoyal, I. et al., "Simplified flow cytometric method for fetal hemoglobin containing red blood cells.", Clinical & Laboratory Hematology, vol. 26, pp. 182-193 (2004).

Amoyal, I., et al., "Flow Cytometric Analysis of Hydroxyurea Effects on Fetal Hemoglobin Production in Cultures of B-Thalassemia Erythroid Precursors", Hemoglobin, vol. 27, No. 2, pp. 77-87 (2003).

Di Liberto, G. et al., "Dense red blood cell and oxygen desaturation in sickle-cell disease.", American Journal of Hematology, vol. 91, No. 18, pp. 1008-1013 DOI: 18.1002/ajs.24467 (2015).

(Continued)

*Primary Examiner* — Maureen Wallenhorst
(74) *Attorney, Agent, or Firm* — ArentFox Schiff LLP

(57) ABSTRACT

The invention concerns a method for determining, by flow cytometry, the hemoglobin content of each erythroid cell of a set of erythroid cells. This method applies in particular to determining the hemoglobin content of each red blood cell of a set of red blood cells. The invention also concerns a method for determining the amount of red blood cells transfused into a patient and for monitoring the therapeutic efficacy of a treatment for sickle cell disease or β-thalassemia.

20 Claims, 13 Drawing Sheets

(56) References Cited

OTHER PUBLICATIONS

Hebert, K., et al., "Fetal Hemoglobin Measurements per Red Blood Cell Provides Biological and Clinical Protective Thresholds", American Society of Hematology, vol. 134, Issue Supplement 1 (Nov. 13, 2019).

Hebert, N., et al., "Individual red blood cell fetal hemoglobin quantification allows to determine protective thresholds in sickle cell disease", Am J Hematol., pp. 1235-1245 (2020).

Mundee, Y. et al., "Flow cytometric method for simultaneous assay of foetal haemoglobin containing red cells, reticulocytes and foetal haemoglobin containing reticulocytes.", Clinical & Laboratory Haematology, vol. 23, pp. 149-154 (2001).

Mundee, Y. et al., "Simplified flow cytometric method for fetal hemoglobin containing red blood cells", Cytometry, Communications in Clinical Cytometry, vol. 42, Issue 6, pp. 389-393 (2008).

Raxotoson, M.G. et al., "Biological parameters predictive of percent dense red blood cell decrease under hydroxyures", Orphanet Journal of Rare Diseases, vol. 10, No. 1, pp. 1-5 doi: 10.1186/s13023-015-0272-3 (2015).

\* cited by examiner

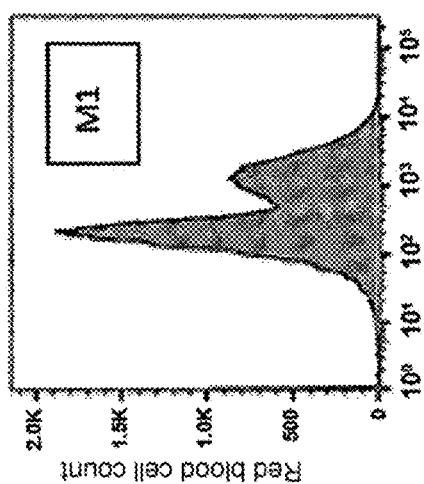
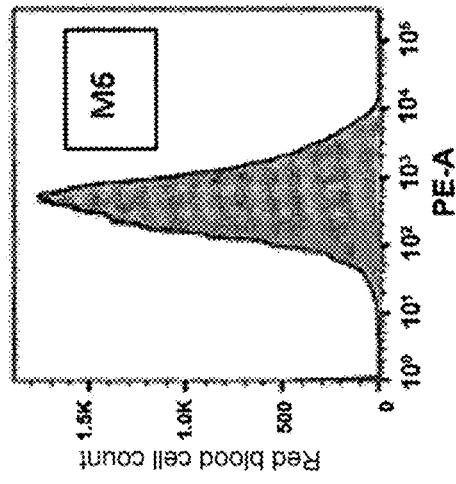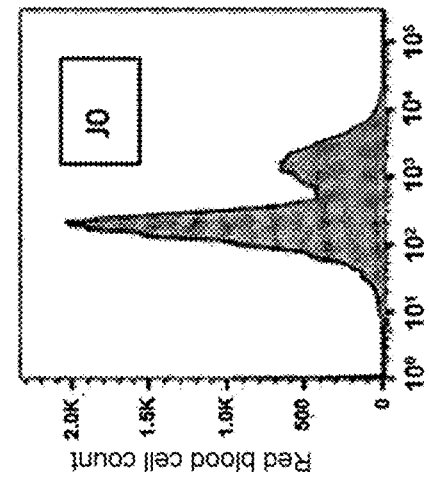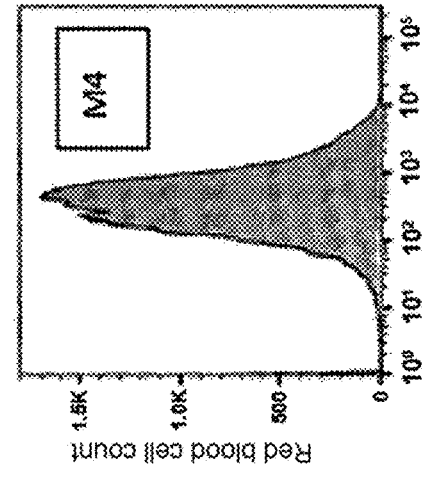

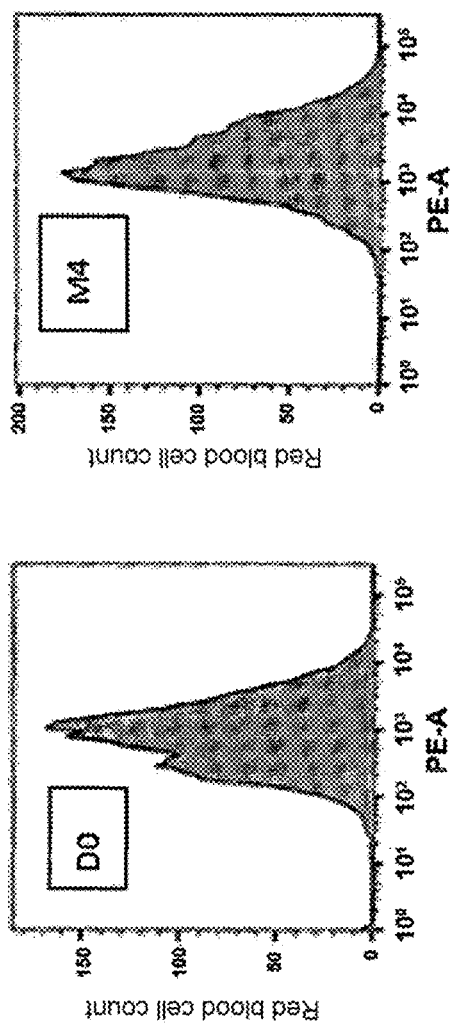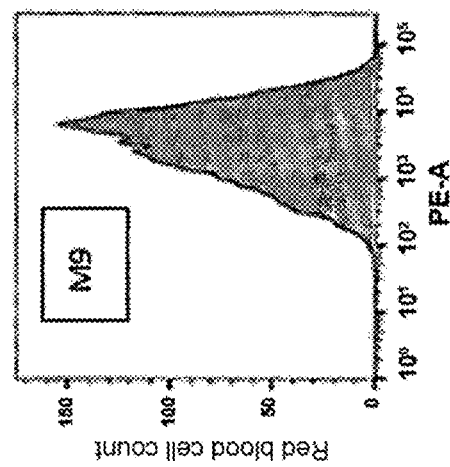

METHOD FOR DETERMINING THE HAEMOGLOBIN CONTENT OF AN ERYTHROID CELL

CROSS-REFERENCE TO RELATED APPLICATIONS

The present application for patent is a Continuation-in-Part of U.S. patent application Ser. No. 16/347,738, filed May 6, 2019, which is a National Stage Entry of International Application PCT/FR2017/053015, filed Nov. 3, 2017, which claims priority to French Patent Application No. 1660713, filed Nov. 4, 2016.

TECHNICAL FIELD

The invention relates to a novel method for determining, in vitro, hemoglobin content of each erythroid cell of a set of erythroid cells, preferably of each red blood cell of a set of red blood cells, by flow cytometry. The invention also relates to a novel method for determining, in vitro, the amount of red blood cells transfused into a patient and to a method for monitoring the therapeutic efficacy of a treatment for sickle cell disease or for β-thalassemia.

TECHNOLOGICAL BACKGROUND

Sickle cell disease is a genetic disease of hemoglobin which was historically characterized by the deformation of red blood cells (RBCs) in response to a decrease in oxygen partial pressure. The red blood cells lose their biconcave (discocyte) shape and are in an elongated, pointed or sickle shape, hence the name sickle cell disease.

Sickle cell disease is due to a mutation of a single nucleotide (GAG→GTG) on codon 6 of the β gene located on the short arm of chromosome 11 (11p 15.5). This mutation results in a structural modification of the hemoglobin β chain which consists of the replacement of glutamic acid in position 6 with a valine so as to form HbS. The major sickle cell syndrome comprises 3 genotypes: a homozygous form (SS), and 2 heterozygous forms (Sβ°Thal and SC which combines the βS mutation and a mutation C characterized by the replacement of the glutamic acid in position 6 with a lysine).

The clinical phenotype of sickle cell disease is characterized, on the one hand, by a large interindividual variability and, on the other hand, by a variability between each event for one and the same patient. The main causes of hospitalization are vaso-occlusive crisis (VOC) and acute chest syndrome (ACS) which can occur at any age. ACS can affect up to 40% of sickle cell disease patients and represents one of the main causes of mortality in adults. Dense red blood cells (DRBCs) and irreversibly sickled cells (ISCs) constitute a subpopulation of SS red blood cells which are highly pathogenic due to their high concentration of HbS which is the main determining factor of polymerization. DRBCs have a high tendency to polymerize and are major factors of the physiopathological mechanisms of sickle cell disease. By virtue of their low deformability combined with a considerable increase in viscosity, DRBCs contribute mainly to the occlusion of the capillaries and the post-capillary venules and to the slowing of blood flow, promoting the appearance of vaso-occlusive phenomena.

In 2010, approximately 5 million carriers of the sickle cell disease trait and 312 000 children with sickle cell disease were counted worldwide, with a high density found in African regions. In 2011, the WHO estimated a prevalence of sickle cell disease trait carriers ranging up to 5% of the worldwide population. Sickle cell disease at the current time represents the most widespread genetic disease in France with a frequency ranging up to 1 birth in 700 in mainland France and 1/2300 with the overseas departments (Bulletin Epidémiologique Hebdomadaire [French Weekly Epidemiological Bulletin] Jul. 3, 2012/May 12, 2015). Mortality rates in children under the age of 5 have decreased considerably over the past few decades due to neonatal screening and to the introduction of preventive treatments for the infections which constitute the main causes of mortality. In France, an improvement in the life expectancy of sickle cell disease patients has also been observed over the past 20 years, with a mortality rate reduced to 35% (Bulletin Epidémiologique Hebdomadaire [French Weekly Epidemiological Bulletin] Mar. 10, 2015). However, the lack of early screening and the limited access to quality treatments and care continue to cause the incidences of mortality in children to increase in developing countries.

The observation of an asymptomatic form of sickle cell disease in SS patients has led to various studies for the purpose of determining the protective effect of at least one hemoglobin, such as hemoglobin F (HbF). This is because the clinical expression of sickle cell disease is attenuated in the perinatal period during which HbF represents the predominant form. A benign form which has genetic traits resulting in an overexpression of HbF is also observed in adults. These patients rarely exhibit a severe clinical manifestation and benefit from a better life expectancy. The protective effect of HbF consists mainly of the inhibition of the formation of the deoxy HbS polymer. Since the polymerization depends essentially on the mean corpuscular hemoglobin concentration (MCHC), the reduction in intracellular concentration of HbS constitutes the principal factor improving clinical expression. In vitro studies carried out on hemoglobin solutions have made it possible to determine the mechanisms of polymerization inhibition by the various hemoglobin variants (HbA, $HbA_2$, HbF, etc.). A more significant inhibitory effect is obtained with HbF. Added to this anti-polymerizing effect is a high oxygen affinity of HbF which provides better protection of the red blood cells. In sickle cell disease patients, HbF is expressed heterogeneously, the protective effect of HbF gives the red blood cells containing a high HbF content a longer lifetime, up to approximately 90 days, while the SS red blood cells which contain little HbF are rapidly eliminated from the general circulation.

To date, increasing the HbF thus constitutes one of the main therapeutic objectives in the treatment of sickle cell disease. Globally, considering the mechanisms of polymerization of HbS, by the aforementioned hemoglobins, measuring the cell content of at least one hemoglobin is also in the purview of the blood monitoring and blood-disease therapeutic objectives, the expression of these hemoglobins being modified by different causes, such as different physiopathologic conditions or therapeutic approaches (including drugs or gene therapy).

Nevertheless, the increase or the decrease of the mean content of an hemoglobin is not always associated with a clinical improvement. For instance, the increase in the mean HbF content is not always associated with a clinical improvement in sickle cell disease patients. Conversely, a clinical improvement may be observed at low mean HbF contents. These observations suggest the existence of a threshold HbF content in each red blood cell, making it possible to inhibit the polymerization of the HbS, and suggest the need to exceed this threshold with, as a result, a more homogeneous distribution of the HbF in the red blood cells, so that each red blood cell benefits from the protective effect of HbF. It has moreover been shown that, in the absence of treatment, the distribution of HbF in the SS red blood cells is heterogeneous. Furthermore, hemoglobins have been reported to exert a protection in other-than sickle-disease pathologies. For instance, hemoglobins S and C have been reported to result in Malaria Protection (Williams T. "How Do Hemoglobins S and C Result in Malaria Protection? "The Journal of Infectious Diseases, Volume 204, Issue 11, 1 Dec. 2011, Pages 1651-1653) and high level of hemoglobin F have been reported to be a prognosis factor for myelodysplastic syndrome (MDS) (Reinhard D, Ann Hemato, March-April 1998; 76(3-4):135-8-Lubbert M, Br J Haematol, 2017 February; 176(4):609-617) Considering the above, the determination of the content of at least one hemoglobin in each red blood cell is thus of essential importance.

Over the past few decades, several techniques have been developed in order to estimate the hemoblobin content, such as the HbF content, of each red blood cell. These techniques were initially based on chemical methods (Betke K, Marti H R, Schlicht I. Estimation of small percentages of foetal hemoglobin. Nature. 1959; 184(Suppl 24):1877-8), then on immunological methods (Navenot J M, Merghoub T, Ducrocq R, Muller J Y, Krishnamoorthy R, Blanchard D. New method for quantitative determination of fetal hemoglobin-containing red blood cells by flow cytometry: application to sickle-cell disease. Cytometry. 1998; 32(3):186-90), the purpose of which was to detect a specific population of red blood cells containing a high HbF content, called "F cells". Although widely used in the diagnosis of fetal-maternal incompatibilities and in the understanding of hemoglobinopathies, these methods are not very sensitive and are limited to a qualitative measurement of F cells (red blood cells positive by immunofluorescence microscopy, immunodiffusion or by flow cytometry, regardless of the HbF expression level). Up until then, the study of the HbF content in each red blood cell was based on this approximative definition of F cells.

There is therefore a real need to develop an easily implemented method for accurately determining the at least one hemoglobin content, such as the HbF content, in each red blood cell of a set of red blood cells in order to be able to explain the clinical response variabilities, to anticipate these clinical response variabilities and thus to adjust the treatment. This would also make it possible to develop new therapeutic approaches for myelodysplastic syndromes (MDS) or blood diseases, such as sickle cell disease, β-thalassemia, said approaches aiming at increasing or decreasing the at least one hemoglobin content in each red blood cell and not only the mean at least one hemoglobin content in a patient.

SUMMARY OF THE INVENTION

The present invention addresses the above needs by supplying a method for determining, in vitro, the content of at least one hemoglobin Hbx in each erythroid cell of a set of erythroid cells contained in a sample of erythroid cells, typically a blood sample, notably a human blood sample. The method according to the invention comprises the steps of:
  a) isolating erythroid cells from the sample;
  b) permeabilizing the membrane of the isolated erythroid cells;
  c) labeling the at least one hemoglobin Hbx of the erythroid cells obtained in step b) with at least one anti-Hbx antibody conjugated to a fluorochrome capable of emitting a fluorescence;
  d) measuring, by flow cytometry, the fluorescence intensity (MFI) of each erythroid cell of the set of erythroid cells;
  e) determining the content of the at least one hemoglobin Hbx in each erythroid cell of the set of erythroid cells by comparing the fluorescence intensity of each red blood cell with a standard curve associating the fluorescence intensity measured for a red blood cell with the at least one hemoglobin Hbx content.

In one embodiment, the membrane of the isolated erythroid cells is fixed before the permeabilization step. In one embodiment, the membrane of the isolated erythroid cells is fixed with sodium azide and/or formaldehyde. In one embodiment, the membrane of the isolated erythroid cells is permeabilized with sodium dodecyl sulfate.

In one embodiment, the fluorochrome is selected from the group consisting of phycoerythrin (PE), fluorescein, isothiocyanate, a derivative thereof or a combination thereof.

The at least one Hbx hemoglobin may be at least one first hemoglobin Hbx1, at least one second hemoglobin Hbx2 and at least one n $n^{th}$ hemoglobin designated as Hbxn. Accordingly, the method comprisessaid method comprising the steps of:
  a) isolating erythroid cells from a sample;
  b) permeabilizing the membrane of the isolated erythroid cells;
  $c_1$) labeling the at least one first hemoglobin Hbx1 of the erythroid cells obtained in step b) with at least one anti-Hbx1 antibody conjugated to a first fluorochrome capable of emitting a first fluorescence; labeling the at least one second hemoglobin Hbx2 of the erythroid cells obtained in step b) with at least one second anti-Hbx2 antibody conjugated to a second fluorochrome capable of emitting a second fluorescence; labeling the at least one $n^{th}$ hemoglobin Hbxn of the erythroid cells obtained in step b) with at least one anti-Hbxn antibody conjugated to a $n^{th}$ fluorochrome capable of emitting a $n^{th}$ fluorescence,
  $d_1$) measuring, by flow cytometry, the fluorescence intensity of each fluorescence emitted by the first, the second, the $n^{th}$ fluorochrome of each erythroid cell of a set of erythroid cells;
  $e_1$) determining the content of the at least one first hemoglobin Hbx1, the at least one second hemoglobin Hbx2, the at least one $n^{th}$ hemoglobin Hbxn in each erythroid cell of the set of erythroid cells by comparing each of the first, the second, the $n^{th}$ fluorescence intensities measured in step $d_1$) with a first, a second and an $n^{th}$ standard curve associating the measured first, second, and $n^{th}$ fluorescence intensities for a red blood cell, with content of the at least one first hemoglobin Hbx1, the content of the at least one second hemoglobin Hb2 and the content of the $n^{th}$ hemoglobin Hbxn.

The at least one Hbx hemoglobin may be n hemoglobins Hbx, designated as Hbxn. Accordingly, the method comprises the steps of:
  a) isolating erythroid cells from a sample;
  b) permeabilizing the membrane of the isolated erythroid cells;
  $c_1$) labeling the at least one first hemoglobin Hbx1 of the erythroid cells obtained in step b) with at least one anti-Hbx1 antibody conjugated to a fluorochrome;

d$_1$) measuring, by flow cytometry, the fluorescence intensity (MFI) of each erythroid cell of a set of erythroid cells;

e$_1$) determining the content of the at least one first hemoglobin Hbx1 in each erythroid cell of the set of erythroid cells by comparing the fluorescence intensity of each red blood cell with a standard curve associating the fluorescence intensity measured for a red blood cell with the first hemoglobin Hbx1 content;

f) iterating the set of steps c$_1$)-e$_1$) for each of the at least one second Hbx2 (steps c$_2$)-e$_2$)), at least one third Hbx3 (steps c$_3$)-e$_3$)) and n$^{th}$ Hbxn (steps c$_n$)-e$_n$)) until the content of the n hemoglobins Hbx in each erythroid cell of the set of erythroid cells is determined.

In one embodiment, the at least one anti-Hbx antibody is directed against at least one of the chains of the at least one hemoglobin Hbx that are selected from the group consisting of α, β, γ, δ, εζ chain, glycosylated derivatives thereof, blood disease variants thereof, mutated forms thereof, or a mixture thereof.

In one specific embodiment, at least one hemoglobin Hbx is selected from the group consisting of HbF (Hemoglobin F), HbA (Hemoglobin A), HbS (Hemoglobin S) and a combination thereof.

In one embodiment, the content of the at least one hemoglobin Hbx is determined for each erythroid cell of a set of at least 10,000 erythroid cells.

In one embodiment, the erythroid cells are red blood cells.

In one embodiment, the content the at least one hemoglobin Hbx in each erythroid cell of the set of erythroid cells is expressed as a concentration relative to the volume of the erythroid cells.

The invention also relates to a method for determining, in vitro, an amount of red blood cells transfused into a patient suffering from sickle cell disease, alpha-thalassemia or beta-thalassemia. Such method comprises the steps of:

a) determining the content of the at least one hemoglobin Hbx selected from the group consisting of HbA, HbF and HbS of each red blood cell of a set of red blood cells of a sample of red blood cells from the patient according to the determining method of any one of the above embodiments directed red blood cells;

b) using the results of step a) to determine the amount of red blood cells transfused into a patient, said transfused red blood cells having an HbF and/or HbS content substantially equal to zero (=0 pg) and or a content ratio of the HbS/(HbF+HbA) substantially equal to zero (=0).

The invention further relates to an in vitro method for monitoring the therapeutic efficacy of a Hematopoietic stem cell transplantation (HSCT) or of a treatment for myelodysplastic syndromes, sickle cell disease or for β-thalassemia, comprising:

a) obtaining a sample containing red blood cells from a patient having undergone a HSCT or a treatment for a myelodysplastic syndrome, sickle cell disease or for β-thalassemia;

b) determining the content of the at least one hemoglobin Hbx in each red blood cell of a set of red blood cells of said sample according to the determining method of any one of the above embodiments directed red blood cells;

c) using the results of step b) in the monitoring of the therapeutic efficacy of Hematopoietic stem cell transplantation (HSCT) or the treatment for sickle cell disease or for β-thalassemia, in which a therapeutic efficacy is observed when at least a predetermined percentage of the red blood cells of the set of red blood cells has a content of the at least one hemoglobin Hbx that increases or decreases at least 2%, at least 5%, at least 7%, at least 10%, at least 12%, at least 15%, or at least 20% compared to the same content prior to the HSCT or the treatment for myelodysplastic syndromes, sickle cell disease or for β-thalassemia.

Lastly, the invention relates to a method for treating sickle cell disease or β-thalassemia, that comprises the steps of:

a) obtaining a sample containing red blood cells from a patient;

b) determining the at least one hemoglobin Hbx content selected from the group consisting of the HbF, HbA and HbS content of each red blood cell of a set of red blood cells of said sample according to the determining method of any one of the above embodiments directed red blood cells;

c) when at least a predetermined percentage of the red blood cells of the set of red blood cells has an HbS content which exceeds a HbS reference threshold, and/or when at least a predetermined percentage of the red blood cells of the set of red blood cells has an HbF and/or HbA content is below HbF and/or HbA reference threshold initiating an appropriate treatment in the patient such as for example a treatment with hydroxyurea and/or erythropoietin.

In one embodiment, at least 20% of the red blood cells of the set of red blood cells have an HbF content which is below the reference threshold. In one embodiment, the reference threshold for HbF may be 2 pg or more, for example 3 pg, for example 4 pg, for example 5 pg, for example 6 pg, for example 7 pg, for example 7.5 pg.

DETAILED DESCRIPTION OF THE INVENTION

Definitions

Human hemoglobins are composed of 4 subunits of polypeptide chains which are identical in pairs. The subunits vary according to the types of hemoglobin and 4 normal hemoglobins can be distinguished in human beings:

embryonic hemoglobins: hemoglobin Gower I (ζ2ε2), hemoglobin Portland (ζ2γ2) and hemoglobin Gower II (α2ε2);

HbF (α2γ2);

adult hemoglobin (HbA) (α2β2);

hemoglobin A2 (HbA2) (α2δ2).

According to one aspect, the above hemoglobins may be qualified as "natural hemoglobins". The term "at least one hemoglobin" designates at least one hemoglobin selected from the group consisting of at least one hemoglobin present in a healthy subject (natural hemoglobin), at least one hemoglobin variant present in a healthy subject, at least one hemoglobin variant present in a subject suffering from a blood disease, a recombinant hemoglobin, and a combination thereof.

In one embodiment, the at least one hemoglobin is selected from the group consisting of at least one hemoglobin present in a healthy subject, at least one hemoglobin variant, typically at least one hemoglobin variant associated with a blood disease, a recombinant hemoglobin, and a combination thereof.

In one embodiment, the at least one hemoglobin variant or the at least one recombinant hemoglobin presents at least one of the α, β, γ, δ, ε and/or r hemoglobin chains.

In one embodiment, the at least one hemoglobin variant or the at least one recombinant hemoglobin presents at least one of the α, β, γ, δ, ε and/or r hemoglobin chains, glycosylated derivatives thereof or mutated forms thereof.

In one embodiment, the at least one hemoglobin is selected from the group consisting of Chain beta A (non-mutated), Chain beta A (non-mutated), Chain beta C (mutated), Chain delta, Chain alpha, Chain epsilon, Chain zeta, glycosylated beta chaine, Hb Providence, HbG philadelphia, HbA2-Coburg, Hb A2-Flatbush, Hb A2-Babinga, Hb A2', Hb Bart's, Hb Stanleyville II, Hb G-Pest, Hb O-Arab, Hb P-Nilotic, Hb Kenya, Hb J Broussais, Hb Winnipeg, Hb Matsue-Oki, Hb Mexico, Hb I, Hb Sétif, Hb J Paris, Hb Savaria, Hb Hasharon, Hb Roanne, Hb Fort de France, Hb Hopkins II, Hb Kurosaki, Hb Grady, Hb Galliera I, Hb Lepore, HbA del-3.7 kB, HBB: c.118>T, HBB: c.92+5G>C IVS-I-5, HBB: c.-138C>T, HBB:c.-79>G HbE, HBB:c.93-21G>A IVS-I-110, HBB:c.315+1G>A IVS-II-1, Lepore-Baltimore, Lepore Boston-Wasington, Hb Alperton (HBB: c.407C>T), Hb Midnapore HBB: c.161C>T, Hb Knossos (HBB:c.82G>T), and Hb G-Makassar.

In one embodiment, the at least one hemoglobin is selected from the group consisting of at least one hemoglobin present in a healthy subject, at least one hemoglobin variant present in a sickle-disease patient, at least one hemoglobin variant present in a patient suffering from α-thalassemia, at least one hemoglobin variant present in a patient suffering from β-thalassemia, at least one hemoglobin variant present in a patient suffering from β-δ-thalassemia, a recombinant hemoglobin, and a combination thereof.

Hemoglobin variants that have been reported to be associated with a disease, notably a blood disease, may be selected from the group consisting of:
Hemoglobin Asharon,
Hemoglobin Barts (γ4),
Hemoglobin C ($α2β^C2$),
Hemoglobin D-Punjab ($α2β^D2$),
Hemoglobin O-Arab,
Hb S Antilles
Hemoglobin E ($α2β^E2$),
Hemoglobin H (β4),
Hemoglobin Hopkins-2,
Hemoglobin S ($α2β^S2$),
Hemoglobin AS,
Hemoglobin SC disease, and
a combination thereof.

"HbA" denotes Hemoglobin A, also known as adult hemoglobin, hemoglobin A1 or α2β2. HbA is the most common human hemoglobin tetramer in healthy subjects, accounting for over 97% of the total red blood cell hemoglobin. Hemoglobin A is the most common adult form of hemoglobin and exists as a tetramer containing two alpha subunits and two beta subunits (α2β2). According to a specific embodiment, "amount and/or concentration of HbA" denotes the the combined amount or concentration of HbA and HbA2.

Hemoglobin Asharon denotes an hemoglobin variant wherein the histidine of the 47 α chain position is substituted by aspartic acid.

"Hb Barts" denotes hemoglobin Barts (γ4), an hemoglobin variant, formed by a tetramer of γ chains, which may be present in variants of α thalassemia.

"HbC" denotes hemoglobin C ($α2β^C2$), an hemoglobin variant due to a variation in the 3-chain gene. This variant causes a mild chronic hemolytic anemia.

"HbD" denotes hemoglobin D-Punjab or D-Los Angeles, an hemoglobin variant due to a variation in the β-chain gene. People with hemoglobin D trait can also have a child with hemoglobin D disease that may cause a mild anemia.

"HbE" denotes hemoglobin E ($α2β^E2$), an hemoglobin variant due to a variation in the β-chain gene. This variant causes a mild chronic hemolytic anemia.

"HbF" denotes hemoglobin F composed of two subunits of α (alpha) chains and two subunits of γ (gamma) chains. HbF is composed of two types of γ chains: Gγ and Aγ which differ in terms of their residue in position 136 corresponding to a glycine for the Gγ chain and an alanine for Aγ. There are two minor forms of HbF, including HbF1 which represents 10% of total hemoglobin in the foetus. It contains a $γ^X$ subunit, the N-terminal end of which is substituted with an acetyl group. Other forms of HbF can be observed but in very small amount.

"HbH" denotes hemoglobin H (β4), an hemoglobin variant, formed by a tetramer of β chains, which may be present in variants of α thalassemia.

"Hb Hop-2" denotes the Hemoglobin Hopkins-2 variant comprising two anormal α chains.

Hb Hop-2 is an hemoglobin variant that is sometimes viewed in combination with Hemoglobin S to produce sickle cell disease.

"HbS" denotes hemoglobin S ($α2β^S2$), variant form of hemoglobin found in people with sickle cell disease. There is a variation in the β-chain gene, causing a change in the properties of hemoglobin, which results in sickling of red blood cells.

"Hb Providence" denotes hemoglobin Providence Asn and Hemoglobin Providence Asp that are two abnormal hemoglobins which arise from a single genetic change in the β chain. In Hb Providence Asn, asparagine is substituted by lysine at position 82 (EF6) Hb Providence Asp appears to be the result of a partial deamidation of the asparagine situated at position β 82.

"HbAS" denotes hemoglobin AS, a heterozygous hemoglobin form causing sickle cell trait with one adult gene and one sickle cell disease gene.

"HbSC" denotes an hemoglobin variant compound presenting heterozygous form with one sickle gene and another encoding Hemoglobin C.

The measurement of at least one hemoglobin in each erythroid cell according to the invention may be expressed as an amount or a concentration of said at least one hemoglobin. For the purposes of the invention, the term "content" should be understood in its main sense, that is to say the amount of the at least one hemoglobin. The content can be expressed as weight content, for example in picograms (pg) per cell. Alternatively or additionally, for the purposes of the invention, the concentration should be understood as the amount in weight of the at least one hemoglobin in each erythroid cell relative to the volume of the erythroid cells, typically, the red blood cells. The content can be expressed for example in picograms (pg) per 100 mL of erythroid cell volume or picograms per fL (femtoliter) of erythroid cell volume.

The erythroid cell volume may be calculated by any means known in the art, such as the methods for calculating the erythroid cell volume described in the U.S. Ser. No. 15/316,106 application that are incorporated herein by reference. Alternatively or additionally, the amount is expressed as the ratio of at least two hemoglobins per cell. In one embodiment, the amount refers to the ratio of HbF/HbS in each cell. In one embodiment, the amount refers to the ratio of HbA/HbS in each cell. In one embodiment, the amount refers to the ratio of (HbF+HbA)/HbS in each cell. In one embodiment, the amount refers to the ratio of the amount of an at least one recombinant hemoglobin on the HbS amount in each cell.

In the context of the present application, the term "content" may also refer to the expression of "concentration" expressing such content relative to the volume of the erythroid cells.

For the purposes of the invention, the expression "the at least one hemoglobin content or concentration of each erythroid cell" denotes the amount of the at least one hemoglobin in each erythroid cell, taken individually. In one embodiment, the content (or amount) is expressed by weight, in picograms (pg). For example, the determination of the at least one hemoglobin content or concentration, such as the HbF content or concentration, of each erythroid cell of a set of 10 erythroid cells corresponds to the obtaining of 10 values of amount of the at least one hemoglobin, corresponding to the content or concentration in the at least one hemoglobin of each of the 10 erythroid cells taken individually.

For the purposes of the invention, the term "erythoid cell" or "erythroid cells" denotes cells which express hemoglobin, for which it is desired to measure the presence of the at least one hemoglobin among a set of said cells. For the purposes of the invention, the "erythroid cells" denote the erythroid cells which differentiate at the late erythropoiesis stage, for example the erythroblasts, the reticulocytes or the red blood cells. Said erythropoiesis cells are cells that may be non-circulating, that is to say derived from the bone marrow (for example the erythroblasts) or circulating cells, that is to say blood cells (for example the reticulocytes or the red blood cells) or cells derived from erythroid cells, for example recombinant erythroid cells. For the purposes of the invention, the erythroid cells are capable of containing the at least one hemoglobin, such as HbF, HbA, HbS, any one of the hemoglobin variants and/or recombinant derivatives of hemoglobin as defined above. In order to avoid any ambiguity, throughout the present description, the terms "erythroid cell" and "erythroid cells" can be respectively replaced, for example, with "red blood cell" or "red blood cells". For example, the invention relates to a method for determining, in vitro, the content or the concentration of at least one hemoglobin, such as hemoglobin F (HbF), in each red blood cell of a set of red blood cells, comprising the steps of:
  a) isolating red blood cells from a sample;
  b) permeabilizing the membrane of the isolated red blood cells;
  c) labeling the at least one hemoglobin (Hbx) of the red blood cells obtained in step b) with an at least one antibody (anti-Hbx) directed to at least one chain ($\alpha$, $\beta$, $\gamma$, $\delta$, $\varepsilon$ and/or $\zeta$) of the at least one hemoglobin (Hbx), said antibody being conjugated to a fluorochrome;
  d) measuring, by flow cytometry, the fluorescence intensity (MFI) of each red blood cell of a set of red blood cells;
  e) determining the content of the at least one hemoglobin of each red blood cell of the set of red blood cells.

It should be understood that "Hbx" denotes at least one hemoglobin, variant and/or recombinant derivative thereof as defined above.

For the purposes of the invention, the expression "set of erythroid cells" corresponds to a set of erythroid cells contained in a sample of erythroid cells. It is possible for the set of erythroid cells to range up to 100% of the erythroid cells present in the sample, that is to say all of the erythroid cells present in the sample. Thus, the set of erythroid cells corresponds to between 100% and 0%, 0% being exclusive, of the erythroid cells present in the sample. In one particular embodiment, the set of erythroid cells comprises at least 10 000 erythroid cells, preferably at least 100 000 erythroid cells, preferably between 50 000 and 100 000 erythroid cells. In this particular embodiment, the hemoglobin content, in particular the hemoglobin F content, is determined for each of the erythroid cells of a set of at least 10 000 erythroid cells, preferably of at least 100 000 erythroid cells, preferably between 50 000 and 100 000 erythroid cells.

For the purposes of the invention, the term "flow cytometry" denotes a technique well known to those skilled in the art which makes it possible to pass particles, molecules or cells at high speed through a laser beam, while counting them and characterizing them. It is the light re-emitted by the particles, molecules or cells (by scattering or fluorescence) which makes it possible to characterize them according to the desired criterion or criteria. Generally, the particles, molecules or cells are labeled with a fluorochrome which absorbs the energy from the laser and which re-emits the absorbed energy in the form of photons of a higher wavelength. In the context of the invention, the re-emitted light is obtained by specific labelling of at least one chain of the at least one hemoglobin, with an at least one fluorochrome-conjugated antibody directed to said at least one chain of the at least one hemoglobin.

It should be understood that an antibody directed to at least one chain, selected from the group consisting of $\alpha$, $\beta$, $\gamma$, $\delta$, $\varepsilon$ and/or r chains and/or variants thereof, of the at least one hemoglobin Hbx is also an antibody (anti-Hbx) directed to the at least one hemoglobin Hbx itself that comprises such at least one chain.

According to one embodiment, the at least one chain of the at least one hemoglobin is selected from the group consisting of the $\alpha$, $\beta$, $\gamma$, $\delta$, $\varepsilon$ and/or r hemoglobin chains, glycosylated derivatives thereof, blood disease variants or mutated forms thereof.

According to exemplary and non-limitative embodiments, the antibody may be selected from the group consisting of:
  anti $\beta$-chain clone: 14G2.G11.F11 clone (Rockland/ThermoFisher®)
  anti $\beta$ (mutated)-chain clone: 15C2.C11.F2.G11 clone (Rockland®)
  anti $\beta$ (HbS mutation)-chain clone: 200 301 GS5. clone (Rockland®)
  anti $\delta$-chain clone: 21G1.F1.B9.G9.D11 clone (Rockland®)
  anti $\alpha$-chain clone: EPR3608 clone (Abcam®) or 200 301 GS4 (Rockland®)
  anti $\varepsilon$-chain clone: PA5-106357 or PA5-96263 clone (ThermoFisher®)
  anti $\zeta$-chain clone: MAB7708 (R&D@)
  anti $\beta$ (glycosylated)-chain clone: AbD15790 (Bio-Rad®)
  anti $\beta$-chain (Hb Providence mutation) clone: as described in the International Journal of Molecular Sciences, 2020, 21, 9453
  anti $\alpha$-chain (Hb Asharon mutation), clone: as described in the Journal of Immunology Methods 1981; 42(1): 35-44
  anti $\gamma$-chain clone: as described in Translational Research Vol165, Issue 6, June 2015, p 689-695, or
  anti $\alpha$-chain (Hb G Philadelphia mutation), as described in Hemoglobin 1988; 12(2):125-36.

In one particular embodiment, the anti $\alpha$-chain clone antibody, such as for example 200 301 GS4 (Rockland®), labels both adult hemoglobin (HbA) and hemoglobin A2 (HbA2), while it does not cross react with HbS or HbF.

In one specific embodiment, the re-emitted light is obtained by specific labeling of the HbF present in the erythroid cells with an anti-HbF antibody conjugated to a fluorochrome.

In one specific embodiment, the re-emitted light is obtained by specific labeling of the HbS present in the erythroid cells with an anti-HbS antibody conjugated to a fluorochrome.

In one specific embodiment, the re-emitted light is obtained by specific labeling of the HbA present in the erythroid cells with an anti-HbA antibody conjugated to a fluorochrome.

According to a variant of this embodiment, the anti-HbA antibody labels both adult hemoglobin (HbA) and hemoglobin A2 (HbA2). According to a variant of this embodiment, the anti-HbA antibody labels both adult hemoglobin (HbA) and hemoglobin A2 (HbA2), without cross-reacting with HbS or HbF.

For the purposes of the invention, the term "fluorochrome" (or "fluorophore") denotes a chemical substance capable of emitting fluorescent light after excitation by a laser. In the context of the invention, the fluorochrome is coupled to an anti-Hbx antibody. Those skilled in the art have available a wide choice of fluorochromes suitable for flow cytometry. All the fluorochromes which can be coupled to an antibody may be used in the context of the present invention. In one particular embodiment, the fluorochrome is fluorescein isothiocyanate (FITC) or phycoerythrin (PE), or a derivative thereof, preferably PE. PE, by virtue of its conformational (steric hindrance) properties has the advantage of having a PE:antibody ratio close to 1. In one specific embodiment the fluorochrome is selected from the group consisting of AlexaFluor®350, AlexaFluor®405, AlexaFluor®430, AlexaFluor®488, AlexaFluor®500, AlexaFluor®532, AlexaFluor®568, AlexaFluor®594, AlexaFluor®633, AlexaFluor®647, AlexaFluor®660, AlexaFluor®680, AlexaFluor®700, AlexaFluor®750, AlexaFluor®790, APC, APC-Cy7, APC-H7, APC-R700, BB515, BB630P2, BB660P2, BB700, BB755P, BB790P, BODIPY® R6G, BODIPY®, BUV395, BUV496, BUV563, BUV615, BUV661, BUV737, BUV805, BV421, BV510, BV570, BV605, BV650, BV711, BV750, BV786, Pacific Blue, PE, PE-Cy5, PE-Cy7, PE-Cy5.5, PERCP, PERCP-Cy5.5, QDot®525, QDot®545, QDot®565, QDot®585, QDot®605, QDot®625, QDot®655, QDot®705, and QDot®800. The antibody coupling chemistries are well known to those skilled in the art and the present invention is not limited to a particular coupling chemistry.

As it is used here, the term "antibody" refers to immunoglobulin molecules or other molecules which comprise at least one antigen-binding domain. It encompasses in particular whole antibodies, fragments of antibodies comprising an antigen-binding domain (e.g. Fab, Fab' and F(ab)2, scFv, fragments comprising either a VL domain or a VH domain), monoclonal antibodies, polyclonal antibodies, chimeric antibodies, humanized antibodies, primatized antibodies, monospecific antibodies, multispecific antibodies, single-chain antibodies (e.g. of camelid type). The antibodies according to the invention may be antibodies of any type, for example IgG, IgE, IgM, IgD, IgA and IgY, of any class, for example IgG1, IgG2, IgG3, IgG4, IgA1 and IgA2 or of any subclass. In one specific embodiment, the at least one anti-Hbx antibody is an anti-HbF antibody, preferably an anti-HbF antibody directed against the gamma (γ) chain of HbF. In one particular embodiment, the antibody is a monoclonal antibody. In one specific embodiment, the at least one anti-Hbx antibody is an anti-HbA antibody, preferably an anti-HbA antibody directed against the alpha (α) chain of HbA. In one specific embodiment, the at least one anti-Hbx antibody is an anti-HbS antibody, preferably an anti-HbF antibody directed against the beta (β) chain of HbS.

Generally, monoclonal antibodies can be obtained by the hybridoma technique, the general principle of which is recalled below. Firstly, an animal, generally a mouse, is immunized with the antigen of interest (for example human HbF) or a fragment of the antigen of interest (for example the gamma chain of human HbF), the B lymphocytes of said animal then being capable of producing antibodies against said antigen. These antibody-producing lymphocytes are then fused with "immortal" myeloma cells (for example murine) in order to give hybridomas. Each hybridoma is multiplied in clone form, each one leading to the production of a monoclonal antibody, the properties of recognition of which, with regard to said antigen of interest, may be tested for example by ELISA, by immunoblotting (Western blot), either one-dimensional or two-dimensional, with immunofluorescence, or using a biosensor. The monoclonal antibodies selected in this way are subsequently purified, especially using the chromatography technique. The monoclonal antibodies may also be recombinant antibodies obtained by genetic engineering by techniques well known to those skilled in the art.

For the purposes of the invention, the term "diagnosis" denotes determining the severity of a disease, typically a blood disease selected from the group of alpha-thalassemia, beta-thalassemia, and sickle cell disease, preferably sickle cell disease in a patient.

For the purposes of the invention, the term "sample" denotes a sample containing erythroid cells, said sample having been obtained from a patient, and from which sample it is possible to carry out the invention. Advantageously, the sample is a blood sample, preferably a human blood sample. The sample may be taken from a patient at any time, for example by taking a blood sample.

For the purposes of the invention, the term "homogeneous patient" denotes a patient who has a homogeneous content of the at least one hemoglobin (Hbx) over all of his or her erythroid cells. The content of the at least one hemoglobin (Hbx) over all of the erythroid cells thus follows a normal logarithmic distribution. A homogeneous subject may be a female pregnant subject and/or a foetus. A homogeneous patient may be a patient presenting a hereditary persistence of HbF, β-thalassemia or β-δ-thalassemia. A homogeneous patient may be a patient presenting a myelodysplastic syndrome (MDS). In a specific embodiment, the term "homogeneous patients" denotes a set of patients each having a homogeneous HbF content over all of their erythroid cells, it being possible for the HbF content to be different from one patient to the other.

For the purposes of the invention, the term "homogeneous sample" denotes a sample of erythroid cells that has been obtained from a homogeneous patient. Thus, the content of the at least one hemoglobin (Hbx) in the erythroid cells of a homogeneous sample exhibits a low variance. That is to say that the content of the at least one hemoglobin (Hbx) in each of the erythroid cells of the homogeneous sample is concentrated around the said at least one hemoglobin (Hbx) content of the homogeneous sample. Advantageously, a low variance is a variance of less than 15%, advantageously less than 10%, less than 9%, 8%, 7%, 6%, 5%, 4%, 3%, 2%, 1%.

Method for Determining the Content of the at Least One Hemoglobin (Hbx) in an Erythroid Cell The inventors have demonstrated that flow cytometry is a particularly suitable technique for easily and accurately determining the content of at least one hemoglobin (Hbx) in each erythroid cell of a set of erythroid cells.

Thus, the invention relates to a method for determining, in vitro, a content of at least one hemoglobin Hbx in each erythroid cell of a set of erythroid cells contained in a sample, comprising the steps of:
  a) isolating erythroid cells from the sample;
  b) permeabilizing the membrane of the isolated erythroid cells;
  c) labeling the at least one hemoglobin (Hbx) of the erythroid cells obtained in step b) with at least one anti-Hbx antibody conjugated to a fluorochrome, capable of emitting fluorescence;
  d) measuring, by flow cytometry, the fluorescence intensity (MFI) of each erythroid cell of a set of erythroid cells;
  e) determining the content of the at least one hemoglobin Hbx in each erythroid cell of the set of erythroid cells, typically by comparing the fluorescence intensity of each red blood cell with a standard curve associating the fluorescence intensity measured for a red blood cell with the at least one hemoglobin Hbx content.

It should be understood that measured fluorescence is emitted by the fluorochrome that is conjugated to the at least one anti-Hbx antibody.

It should be further understood that at least one hemoglobin Hbx may denote at least one first hemoglobin Hbx1, at least one second hemoglobin Hbx2, at least one third hemoglobin Hbx3, at least one fourth hemoglobin Hbx4, or at least one $n^{th}$ hemoglobin Hbxn; the number n being a non-zero natural number, i.e 1, 2, 3, 4, 5, 6 . . . n.

In one embodiment, at least one hemoglobin (Hbx) denotes at least one first hemoglobin Hbx1, at least one second hemoglobin Hbx2, and at least one third hemoglobin Hbx3.

In one embodiment, at least one hemoglobin (Hbx) denotes at least one first hemoglobin Hbx1, and least one second hemoglobin Hbx2.

Likewise, it should be understood that at least one anti-Hbx antibody may denote at least one first anti-Hbx1 antibody, at least one second anti-Hbx2 antibody, at least one third hanti-Hbx3 antibody, at least one fourth anti-Hbx4 antibody, or at least one $n^{th}$ anti-HbXn antibody; the number n being a non-zero natural number.

In one embodiment, at least one anti-Hbx antibody denotes at least one first anti-Hbx1 antibody, at least one second anti-Hbx2 antibody, and at least one third anti-Hbx3 antibody.

In one embodiment, at least one anti-Hbx antibody denotes at least one first anti-Hbx1 antibody and at least one second anti-Hbx2 antibody.

In one specific embodiment, each independently of the at least one hemoglobin Hbxn is selected from the group consisting of HbF, HbA, HbS and a combination thereof. According to such embodiment, each independently of the at least one anti-Hbxn antibody is selected from the group consisting of anti-HbF antibody, anti-HbA antibody, anti-HbS antibody and a combination thereof.

According to a first variant of the method, the determination of the content of at least one hemoglobin Hbxn and the content of the at least one hemoglobin Hbxn-1 are carried out simultaneously. According to such variant, the fluorochrome of the anti-Hbxn-1 conjugated antibody emits at a different wavelength from the emission wavelength of the fluorochrome of the anti-Hbxn conjugated antibody. In one embodiment, the emission wavelength of the anti-Hbxn-1 conjugated fluorochrome overlaps less than 20%, less than 15%, les than 10%, less than 10%, less than 5%, less than 2%, less than 1%, less than 0.5% or less than 0.1% with the emission wavelength of the anti-Hbxn conjugated fluorochrome.

In one embodiment according to the first variant, the method comprises the steps of:
  a) isolating erythroid cells from a sample;
  b) permeabilizing the membrane of the isolated erythroid cells;
  c) labeling the at least one first hemoglobin Hbx1 of the erythroid cells obtained in step b) with at least one anti-Hbx1 antibody conjugated to a fluorochrome; and further labeling at least one second hemoglobin Hbx2 with at least one anti-Hbx2 antibody conjugated to a fluorochrome (step $c_2$)), and a $n^{th}$ hemoglobin Hbxn with at least one anti-Hbxn antibody conjugated to a fluorochrome (step $c_n$));
  d) measuring, by flow cytometry, the fluorescence intensity (MFI) of each erythroid cell of a set of erythroid cells;
  e) determining the content of the at least one first hemoglobin Hbx1, the at least one second hemoglobin Hbx2, and the $n^{th}$ hemoglobin Hbxn in each erythroid cell of the set of erythroid cells.

In one embodiment according to the first variant, the method comprises the steps of:
  a) isolating erythroid cells from a sample;
  b) permeabilizing the membrane of the isolated erythroid cells;
  c) labeling the at least one first hemoglobin Hbx1 of the erythroid cells obtained in step b) with at least one anti-Hbx1 antibody conjugated to a fluorochrome; and further labeling at least one second hemoglobin Hbx2 with at least one anti-Hbx2 antibody conjugated to a fluorochrome (step $c_2$)), and at least one third hemoglobin Hbx3 with at least one anti-Hbx3 antibody conjugated to a fluorochrome (step $c_3$))
  d) measuring, by flow cytometry, the fluorescence intensity (MFI) of each erythroid cell of a set of erythroid cells;
  e) determining the content of the at least one first hemoglobin Hbx1, the at least one second hemoglobin Hbx2, the at least one third hemoglobin Hbx3 in each erythroid cell of the set of erythroid cells.

In one embodiment according to the first variant, the method comprises the steps of:
  a) isolating erythroid cells from a sample;
  b) permeabilizing the membrane of the isolated erythroid cells;
  c) labeling the at least one first hemoglobin Hbx1 of the erythroid cells obtained in step b) with at least one anti-Hbx1 antibody conjugated to a first fluorochrome; and further labeling at least one second hemoglobin Hbx2 with at least one anti-Hbx2 antibody conjugated to a second fluorochrome (step $c_2$)), and a third hemoglobin Hbx3 with at least one anti-Hbx3 antibody conjugated to a third fluorochrome (step $c_3$));
  d) measuring, by flow cytometry, the fluorescence intensity (MFI) of each erythroid cell of a set of erythroid cells;
  e) determining the content of the at least one first hemoglobin Hbx1, the at least one second hemoglobin Hbx2, and the third hemoglobin Hbx3 in each erythroid cell of the set of erythroid cells.

In one embodiment according to the first variant, the method comprises the steps of:
a) isolating erythroid cells from a sample;
b) permeabilizing the membrane of the isolated erythroid cells;
   $c_1$) labeling the at least one first hemoglobin Hbx1 of the erythroid cells obtained in step b) with at least one anti-Hbx1 antibody conjugated to a first fluorochrome capable of emitting a first fluorescence; labeling the at least one second hemoglobin Hbx2 of the erythroid cells obtained in step b) with at least one anti-Hbx2 antibody conjugated to a second fluorochrome capable of emitting a second fluorescence; labeling the at least one $n^{th}$ hemoglobin Hbxn of the erythroid cells obtained in step b) with at least one anti-Hbxn antibody conjugated to a $n^{th}$ fluorochrome capable of emitting a $n^{th}$ fluorescence,
   $d_1$) measuring, by flow cytometry, the fluorescence intensity of each fluorescence emitted by the first, the second, the $n^{th}$ fluorochrome of each erythroid cell of a set of erythroid cells;
   $e_1$) determining the content of the at least one first hemoglobin Hbx1, the at least one second hemoglobin Hbx2, the at least one $n^{th}$ hemoglobin Hbxn in each erythroid cell of the set of erythroid cells, typically by comparing each of the first, the second, the $n^{th}$ fluorescence intensity measured in step $d_1$) with a first, a second and an $n^{th}$ standard curve associating the measured first, second, and $n^{th}$ fluorescence intensity for a red blood cell with content of the at least one first hemoglobin Hbx1, the content of the at least one second hemoglobin Hb2 and the content of the $n^{th}$ hemoglobin Hbxn.

In one specific embodiment according to the first variant, the method comprises the steps of:
a) isolating erythroid cells from a sample;
b) permeabilizing the membrane of the isolated erythroid cells;
c) labeling the hemoglobin F (HbF) of the erythroid cells obtained in step b) with at least one anti-HbF antibody conjugated to a fluorochrome; and further labeling hemoglobin A (HbA) with at least one anti-HbA antibody conjugated to a fluorochrome (step $c_2$)), and a hemoglobin S (HbS) with at least one anti-HbS antibody conjugated to a fluorochrome (step $c_3$));
d) measuring, by flow cytometry, the fluorescence intensity (MFI) of each erythroid cell of a set of erythroid cells;
e) determining the content of HbF, HbA and HbS in each erythroid cell of the set of erythroid cells.

In a specific embodiment of the first variant of the method, the at least one hemoglobin Hbx is selected from the group consisting of HbF, HbS and HbA, and the method comprises the steps of:
a) isolating erythroid cells from a sample;
b) permeabilizing the membrane of the isolated erythroid cells;
   $c_1$) labeling HbF of the erythroid cells obtained in step b) with at least one anti-HbF antibody conjugated to a first fluorochrome; further labeling the HbS with at least one anti-HbS antibody conjugated to a second fluorochrome; further labeling the the HbA with at least one anti-HbA antibody conjugated to a third fluorochrome; preferably each of the first, second and third fluorochrome emitting a fluorescence,
   $d_1$) measuring, by flow cytometry, the fluorescence intensity of each fluorescence emitted by the first, the second, the third fluorochrome of each erythroid cell of a set of erythroid cells;
   $e_1$) determining the content of the HbF, HbS and HbA in each erythroid cell of the set of erythroid cells.

According to a second variant of the method, the determination of the content of at least one hemoglobin Hbxn and the content of the at least one hemoglobin Hbxn-1 are carried out sequentially.

In one embodiment according to the second variant, the method comprises the steps of:
a) isolating erythroid cells from a sample;
b) permeabilizing the membrane of the isolated erythroid cells;
   $c_1$) labeling the at least one first hemoglobin Hbx1 of the erythroid cells obtained in step b) with at least one anti-Hbx1 antibody conjugated to a fluorochrome;
   $d_1$) measuring, by flow cytometry, the fluorescence intensity (MFI) of each erythroid cell of a set of erythroid cells;
   $e_1$) determining the content of the at least one first hemoglobin Hbx1 in each erythroid cell of the set of erythroid cells.
f) iterating the set of steps $c_1$)-$e_1$) for each of the at least one second Hbx2 (steps $c_2$)-$e_2$)), at least one third Hbx3 (steps $c_3$)-$e_3$)) and $n^{th}$ Hbxn (steps $c_n$)-$e_n$)) until the content of the n hemoglobins Hbx in each erythroid cell of the set of erythroid cells is determined.

In one embodiment, the isolated and permeabilized erythroid cells are divided in at least two, at least three or n fractions (aliquots) and each of the set of steps ((steps $c_1$)-$e_1$), ((steps $c_2$)-$e_2$) . . . (steps $c_n$)-$e_n$)) is carried out on the respective fraction 1, fraction 2 . . . fraction n of the isolated and permeabilized erythroid cells obtained in step b).

According to one exemplary embodiment, at least one Hbx refers to three hemoglobins Hbx1, Hbx2 and Hbx3, and the method is for determining, in vitro, the content of three hemoglobins Hbx1-Hbx3 in each erythroid cell of a set of erythroid cells, comprising the steps of:
a) isolating erythroid cells from a sample;
b) permeabilizing the membrane of the isolated erythroid cells;
   $c_1$) labeling the first hemoglobin Hbx1 of in a first fraction of the erythroid cells obtained in step b) with at least one anti-Hbx1 antibody conjugated to a fluorochrome;
   $d_1$) measuring, by flow cytometry, the fluorescence intensity (MFI) of each erythroid cell of a set of erythroid cells;
   $e_1$) determining the content of the first hemoglobin Hbx1 in each erythroid cell of the set of erythroid cells, then
   $c_2$) labeling the second hemoglobin Hbx2 of in a second fraction of the erythroid cells obtained in step b) with at least one anti-Hbx2 antibody conjugated to a fluorochrome;
   $d_2$) measuring, by flow cytometry, the fluorescence intensity (MFI) of each erythroid cell of a set of erythroid cells;
   $e_2$) determining the content of the second hemoglobin Hbx2 in each erythroid cell of the set of erythroid cells, then
   $c_3$) labeling the third hemoglobin Hbx3 of in a first fraction of the erythroid cells obtained in step b) with at least one anti-Hbx3 antibody conjugated to a fluorochrome;

$d_3$) measuring, by flow cytometry, the fluorescence intensity (MFI) of each erythroid cell of a set of erythroid cells;

$e_3$) determining the content of the third hemoglobin Hbx3 in each erythroid cell of the set of erythroid cells.

Step a) consists in isolating erythroid cells from a sample. This step consists in purifying (or increasing the level of purity) of the erythroid cells from a sample comprising erythroid cells.

This step makes it possible in particular to eliminate certain elements (e.g. platelets and white blood cells) that may be present in the sample. Advantageously, the sample is a blood sample, preferably a human blood sample. Numerous techniques are at the disposal of those skilled in the art for isolating erythroid cells from a sample containing erythroid cells.

These techniques are generally simple to carry out and generally provide no particular difficulty to those skilled in the art who will know how to adapt them for their use in the present invention. Mention may for example be made of centrifugation, chromatography techniques, or density gradient fractionation. For example, (i) a blood sample is centrifuged, (ii) the pellet (containing the erythroid cells) is collected and (iii) a suitable isotonic buffer (for example a phosphate buffer) is added to the pellet so as to obtain a suspension of erythroid cells, it being possible for steps (i) to (iii) to be repeated one or more times in order to obtain the isolated erythroid cells.

Step b) consists in permeabilizing the membrane of the isolated erythroid cells. This step consists in rendering the membrane of the erythroid cells sufficiently permeable so that the anti-Hbx antibody can penetrate into the erythroid cells, while at the same time preserving the integrity of the erythroid cells (without red blood cell lysis). Numerous techniques are at the disposal of those skilled in the art for permeabilizing the membrane of the erythroid cells. These techniques are generally simple to carry out and generally provide no particular difficulty to those skilled in the art who will know how to adapt them for their use in the present invention. Mention may for example be made of the use of a chemical agent, such as a detergent and/or a surfactant (e.g. saponin, SDS and/or Triton). In one particular embodiment, the membrane of the isolated erythroid cells is permeabilized with sodium dodecyl sulfate (SDS). SDS, also known as sodium lauryl sulfate (SLS), is a detergent and surfactant which is strong and ionic, and commonly used. Generally, the sodium dodecyl sulfate is simply added to the erythroid cell suspension.

Generally, in one particular embodiment, the membrane of the isolated erythroid cells is fixed before the permeabilization step. The fixing of the erythroid cell membrane makes it possible to prevent (or to limit) the lysis of the erythroid cells during the permeabilization step. Several chemical compounds are at the disposal of those skilled in the art for fixing the membrane of the erythroid cells. In one particular embodiment, the membrane of the isolated erythroid cells is fixed with sodium azide and/or formaldehyde. Generally, the sodium azide and/or formaldehyde are simply added to a pellet of erythroid cells or to a suspension of erythroid cells.

Step c) consists in labeling the at least one hemoglobin Hbx of the erythroid cells obtained in step b) (that is to say the isolated erythroid cells of which the membrane is permeabilized) or a fraction (aliquot) thereof with an anti-Hbx antibody conjugated to a fluorochrome (also hereinafter referred to as "anti-Hbx antibody"). Advantageously, step c) is carried out under conditions which allow intracellular binding between the anti-Hbx antibody and the Hbx.

This step makes it possible to obtain "labeled erythroid cells". Preferably, a sufficient amount of anti-Hbx antibody to label all of the at least one Hbx is used, for example an excess of the at least one anti-Hbx antibody is used. In particular, the step c) consists in labeling the at least one Hbx of the erythroid cells obtained in step b) with an at least one anti-Hbx antibody conjugated to a fluorochrome under conditions which allow intracellular binding between the anti-Hbx antibody and the Hbx. That is to say that the binding between the at least one anti-Hbx antibody and the at least one Hbx takes place inside the erythroid cell. Generally, the labeling consists in incubating the erythroid cells, the membrane of which was permeabilized, with the at least one anti-Hbx antibody for a period of time sufficient to allow intracellular binding between the at least one anti-Hx antibody and the at least one hemoglobin Hbx. The period of time is generally a few minutes, for example between 5 min and 20 min.

In one particular embodiment, the erythroid cells are washed after the labeling step. The washing makes it possible to eliminate the at least one anti-Hbx antibodies not bound to the at least one hemoglobin Hbx. The washing can be carried out with a suitable buffer, for example a PBS buffer. The washing also makes it possible to eliminate the chemical agent that was used to permeabilize the membrane of the red blood cells. The red blood cells thus washed are then used in the flow cytometry measuring step.

According to the second variant of the invention detailed above, the step c) refers to each of the steps $c_1$-$c_n$. According to the exemplary embodiment of the second variant of the invention detailed above, the step c) refers to each of the steps $c_1$-$c_3$.

Step d) consists in measuring, by flow cytometry, the fluorescence intensity (MFI) of each erythroid cell of a set of erythroid cells capable of being emitted by the labeling of step c).

In one embodiment, the at least one labelled Hbx of step c) emits at least one fluorescence (wavelength) whose intensity is measured in step d) for each erythroid cell of the set of erythroid cells. Advantageously, the fluorescence intensity (MFI) of each erythroid cell of the set of erythroid cells is measured independently of the fluorescence intensity (MFI) of the other erythroid cells of the set of erythroid cells. In this step, a set of labeled erythroid cells, that is to say all or some of the labeled erythroid cells, is thus analyzed by flow cytometry. Thus, the fluorescence intensity (MFI) of each erythroid cell of the set of erythroid cells is measured independently of the fluorescence intensity (MFI) of the other erythroid cells of the set of erythroid cells. The fluorescence intensity of each of the erythroid cells taken independently is thus measured in this step. In one particular embodiment, the fluorescence intensity (MFI) is measured for each erythroid cell of a set of at least 10 000 erythroid cells, preferably of at least 100 000 erythroid cells, preferably between 50 000 and 100 000 erythroid cells. It should be understood that measured fluorescence intensity is emitted by the fluorochrome that is conjugated to the at least one anti-Hbx antibody that is itself bound to the at least one hemoglobin Hbx of each erythroid cell.

According to the second variant of the invention detailed above, the step d) refers to each of the steps $d_1$-dn. According to the exemplary embodiment of the second variant of the invention detailed above, the step d) refers to each of the steps $d_1$-$d_3$.

Step e) consists in determining the content of the at least one hemoglobin Hbx in each red blood cell of the set of red blood cells. The content of at least one Hbx is determined from the fluorescence intensity measured by flow cytometry. Advantageously, the content of the at least one hemoglobin Hbx in each erythroid cell of the set of erythroid cells is determined independently of the content of the at least one hemoglobin Hbx of the other erythroid cells of the set of erythroid cells. Thus, the content of the at least one hemoglobin Hbx in each red blood cell of the set of red blood cells is determined independently of content of the at least one hemoglobin Hbx in the other red blood cells of the set of red blood cells. The determination of the content of the at least one hemoglobin Hbx in each red blood cell of the set of red blood cells is carried out by comparing the fluorescence intensity of each red blood cell with a standard curve. The standard curve makes it possible to associate the fluorescence intensity measured for a red blood cell with content of the at least one hemoglobin Hbx.

For example, the standard curve can be obtained in the following way:
- a calibration straight line which makes it possible to correlate a fluorescence intensity with a fluorophore number is established. For example, beads conjugated with a known amount of fluorophore (calibrated beads) can be used. This calibration straight line makes it possible to determine the amount of fluorophore per erythroid cell (hereinafter fluorophore/erythroid cell). Thus, by relating the measurement of the fluorescence intensity of each erythroid cell to the calibration straight line, it is then possible to deduce the amount of fluorophore of each erythroid cell. The fluorophore: antibody ratio (which may be 1:1), may also be used to deduce the number of antigens of each erythroid cell, that is to say the number of Hbx molecules of each erythroid cell;
- the mean content of the at least one hemoglobin Hbx per erythroid cell (MCHbxCo) of a blood sample obtained from patients having an Hbx content that is perfectly homogeneous over all of their erythroid cells ("homogeneous patients") is determined. The Hbx content over all of these erythroid cells follows more precisely a normal logarithmic distribution. These samples are hereinafter referred to as "homogeneous samples". When the erythroid cells are red blood cells, the homogeneous patients are for example patients exhibiting a hereditary persistence of HbF or β-thalassemia or β-δ-thalassemia. For example, it is possible:
  - to determine the mean percentage of the at least one hemoglobin Hbx (that is to say the proportion of the at least one hemoglobin Hbx relative to the entirety of all the hemoglobins, expressed as %) of several homogeneous samples having an Hbx content per erythroid cell which is entirely different from one sample to the other, for example by high-performance liquid chromatography (HPLC). This mean percentage of the at least one hemoglobin Hbx can for example be calculated from HPLC chromatograms by applying the formula: % Hbx=(AUC Hbx/AUC total Hb)×100
  where % Hbx represents the mean percentage of the at least one hemoglobin Hbx over all of the erythroid cells,
  AUC Hbx represents the area under the curve of the at least one hemoglobin Hbx on the chromatogram,
  AUC total represents the sum of the areas under the curves of each type of hemoglobin;
  - to determine the mean hemoglobin content (that is to say all the hemoglobins) per erythroid cell (MCHCo) of the homogeneous samples. For this, the concentration of hemoglobin expressed per liter of blood (for example obtained with a blood hemogram) is divided by the number of erythroid cells per liter of blood (for example obtained by counting the erythroid cells);
  - to determine the mean content of the at least one hemoglobin Hbx per erythroid cell of a homogeneous sample according to the following formula: MCHbxCo=(% Hbx*MCHCo)/100;
- the standard curve is established by associating MCHbxCo and a measurement of the calibrated fluorescence intensity of fluorophore/erythroid cell.

Advantageously, the comparison of the fluorescence intensity of each erythroid cell, standardized relative to the amount of fluorophores, with a standard curve (i.e. obtained from homogeneous samples), makes it possible to determine the content of the at least one hemoglobin Hbx in each erythroid cell in an automated manner. To do this, use is made of the formula given by the linear regression associating the amount of fluorophores per erythroid cell and the MCHxFCo of the homogeneous patients. In one embodiment, use is made of the formula given by the polyonym regression associating the amount of fluorophores per erythroid cell and the MCHxFCo of the homogeneous patients.

For example, the automation of the comparison of the fluorescence intensity of each red blood cell with a standard curve may be carried out by means of a computer system processor. This computer system may comprise computer memory means in which are stored instructions which, when they are executed by the processor of the computer system, will perform the comparison of the fluorescence intensity of each red blood cell with a standard curve in order to provide the distribution of red blood cells regarding their content of Hbx, the percentage of red blood cells having reached a certain threshold of Hb content, or a ratio of all the Hbx content.

Generally, those skilled in the art know how to adjust the parameters of the flow cytometry with the data from the standard curve so as to directly obtain the Hbx content of each erythroid cell of the analyzed set of erythroid cells. The flow cytometry will thus be able to automatically categorize the erythroid cells as a function of their content of the at least one hemoglobin Hbx.

According to the second variant of the invention detailed above, the step e) refers to each of the steps $e_1$-$e_n$. According to the exemplary embodiment of the second variant of the invention detailed above, the step e) refers to each of the steps $e_1$-$e_3$.

Determination of the Amount of Red Blood Cells Transfused into a Patient

The invention also relates to a method for determining, in vitro, the amount of red blood cells transfused into a patient, typically a patient suffering from sickle cell disease or beta-thalassemia, said method comprising:
a) obtaining a sample containing red blood cells from the patient;
b) determining the content of the at least one hemoglobin Hbx selected from the group consisting of HbA, HbF and HbS, of each red blood cell of a set of red blood cells of said sample according to the method of the invention applied to the red blood cells;
c) using the results of step b) to determine the amount of red blood cells transfused into a patient, said transfused red blood cells having an HbF and or HbS content substantially equal to zero (=0 pg) and/or a ratio of the amount HbS/(HbF+HbA) substantially equal to zero (=0).

A content substantially equal to zero (=0 pg) may refer to an amount inferior or equal to 0.05, 0.03, 0.02, or 0.01 pg. a ratio of the amount HbS/(HbF+HbA) substantially equal to zero (=0) may refer to said ratio value inferior or equal to 0.05, 0.005, 0.003, 0.002, or 0.001

According to this method of the invention, the red blood cells can be categorized into two very distinct categories. A category of red blood cells containing variable amounts of HbF and/or HbS/(HbF+HbA) amount ratio (corresponding to the red blood cells of the patient, amount >0 pg and/or ratio substantially more than 0 as detailed above) and a category of red blood cells not containing HbF (corresponding to the transfused red blood cells amount=0 pg) and/or an amount ratio of HbS/(HbF+HbA) substantially equal to 0, as defined above.

In one particular embodiment, the patient is suffering from sickle cell disease or 3-thalassemia.

Advantageously, the amount of transfused red blood cells makes it possible to determine a percentage of transfused red blood cells relative to the total red blood cells of the patient. This makes it possible in particular to monitor the change in the amount of transfused red blood cells (or in the percentage of transfused red blood cells) and thus transfusion to assess the transfusion performance and/or transfusion complications, such as hemolysis of patient/donor red blood cells.

Monitoring of the Therapeutic Efficacy in Blood Diseases

The invention also relates to an in vitro method for monitoring the therapeutic efficacy of a Hematopoietic stem cell transplantation (HSCT) or of a treatment for myelodysplastic syndromes, sickle cell disease or for β-thalassemia, comprising:
  a) obtaining a sample containing red blood cells from a patient having undergone a HSCT or a treatment for a myelodysplastic syndrome, sickle cell disease or for β-thalassemia;
  b) determining the content of the at least one hemoglobin Hbx in each red blood cell of a set of red blood cells of said sample according to the method of the invention applied to the red blood cells;
  c) using the results of step b) in the determination of the therapeutic efficacy of the treatment for sickle cell disease or for β-thalassemia, in which a therapeutic efficacy is observed when at least a predetermined percentage of the red blood cells of the set of red blood cells has a content of the at least one hemoglobin Hbx that increases or decreases at least 2%, at least 5%, at least 7%, at least 10%, at least 12%, at least 15%, or at least 20% compared to the same content prior to the HSCT or the treatment for myelodysplastic syndromes, sickle cell disease or for β-thalassemia.

In one embodiment, the predetermined percentage of the red blood cells of the set of red blood cells is at least 5%, at least 10%, at least 15%, at least 20%, at least 25%, or at least 30% of the set of red blood cells.

In one embodiment, a therapeutic efficacy is observed when at least a predetermined percentage of the red blood cells of the set of red blood cells has an HbF content which exceeds a reference threshold and/or when a decrease in the amount of red blood cells having an HbF content <2 pg is observed. In one particular embodiment, the reference threshold is 2 pg or more, for example 3 pg, for example 4 pg, for example 5 pg, for example 6 pg, for example 7 pg, for example 7.5 pg (that is to say 7.5 pg of HbF in the red blood cell).

In one embodiment, a therapeutic efficacy is observed when at least a predetermined percentage of the red blood cells of the set of red blood cells has an HbS content which is below a reference threshold and/or when an increase in the amount of red blood cells having an HbS content <1 pg is observed. In one particular embodiment, the reference threshold is 1 pg or less, for example 0.5 pg, for example 0.1 pg, for example 0.05 pg, for example 0.005 pg, for example 0.001 pg, for example 0 pg HbS (that is to say no detectable HbS in the red blood cell).

Thus, it is possible to monitor the progression in the therapeutic efficacy of HSCT or a treatment as defined above, aiming at increasing HbF and/or HbA, for HSCT, sickle cell disease or for β-thalassemia treatment over time, before, during or after the treatment of the patient. It is also possible to monitor the progression in the therapeutic efficacy of HSCT or a treatment as defined above, aiming at decreasing HbS, before, during or after the treatment of the patient. In one specific embodiment, it is possible to monitor the progression in the therapeutic efficacy of a treatment, aimed at increasing HbF, for sickle cell disease or for β-thalassemia over time, before, during or after the treatment of the patient. It is thus possible to monitor the progression of the therapeutic efficacy of known treatments, or of new treatments. It is thus possible to identify new treatments for myeloid dysplasia or blood diseases such as sickle cell disease or β-thalassemia which make it possible to increase or decrease the content of the at least one Hbx as detailed above.

The invention also relates to an in vitro method for monitoring the therapeutic efficacy of a treatment comprising the administration of at least one hemoglobin Hbx, typically a synthetic hemoglobin Hbx, comprising:
  a) obtaining a sample containing red blood cells from a patient having undergone a treatment comprising the administration of at least one hemoglobin Hbx, typically a synthetic hemoglobin Hbx;
  b) determining the content of the at least one hemoglobin Hbx in each red blood cell of a set of red blood cells of said sample according to the method of the invention applied to the red blood cells;
  c) using the results of step b) in the determination of the therapeutic efficacy of the treatment, in which a therapeutic efficacy is observed when at least a predetermined percentage of the red blood cells of the set of red blood cells, typically at least 5%, at least 10%, at least 15%, at least 20%, at least 25%, or at least 30% of the set of red blood cells, has a content of the at least one hemoglobin Hbx that increases at least 2%, at least 5%, at least 7%, at least 10%, at least 12%, at least 15%, or at least 20% compared to the same content prior to the treatment.

Method for Treating Blood Diseases

The invention also relates to a method for treating sickle cell disease or β-thalassemia, comprising:
  a) obtaining a sample containing red blood cells from a patient;
  b) determining the at least one hemoglobin Hbx content selected from the group consisting of the HbF, HbA and HbS content of each red blood cell of a set of red blood cells of said sample according to the method of the invention applied to the red blood cells;
  c) when at least a predetermined percentage of the red blood cells of the set of red blood cells, typically at least 10%, at least 20%, at least 30%, at least 40%, at least 45%, or at least 50% of the set of red blood cells, has an HbS content which exceeds a HbS reference threshold, and/or when at least a predetermined percentage of the red blood cells of the set of red blood cells has an HbF and/or HbA content is below HbF and/or HbA reference threshold, initiating an appropriate treatment in the patient.

For example, the need to treat a patient or not treat said patient can be evaluated. It is also possible to choose the treatment that will be most suitable for the patient. It is thus possible to be sure that the patient receives the most suitable treatment.

In one particular embodiment, at least 50% of the red blood cells of the set of red blood cells have an HbF content which exceeds the reference threshold.

In one particular embodiment, the reference HbF threshold is 2 pg or more, for example 3 pg, for example 4 pg, for example 5 pg, for example 6 pg, for example 7 pg, for example 7.5 pg (that is to say 7.5 pg of HbF in the red blood cell). The article by Steinberg et al. (Blood 2014, 123, 481-485) gives information on the detectable HbF thresholds.

In one particular embodiment, the reference HbF threshold is 1 pg or less, for example 0.5 pg or less, for example 0.1 pg or less, for example 0.05 pg or less, for example 0.005 pg or less, for example 0.001 pg or less, for example 0 pg HbS (that is to say no detectable HbS in the red blood cell).

In one particular embodiment, the suitable treatment is hydroxyurea and/or erythropoietin.

The signal measured is the area under the curve (A for area) of the variations in fluorescence intensities of each cell. Along the ordinate: red blood cell count.

Figure 2A:
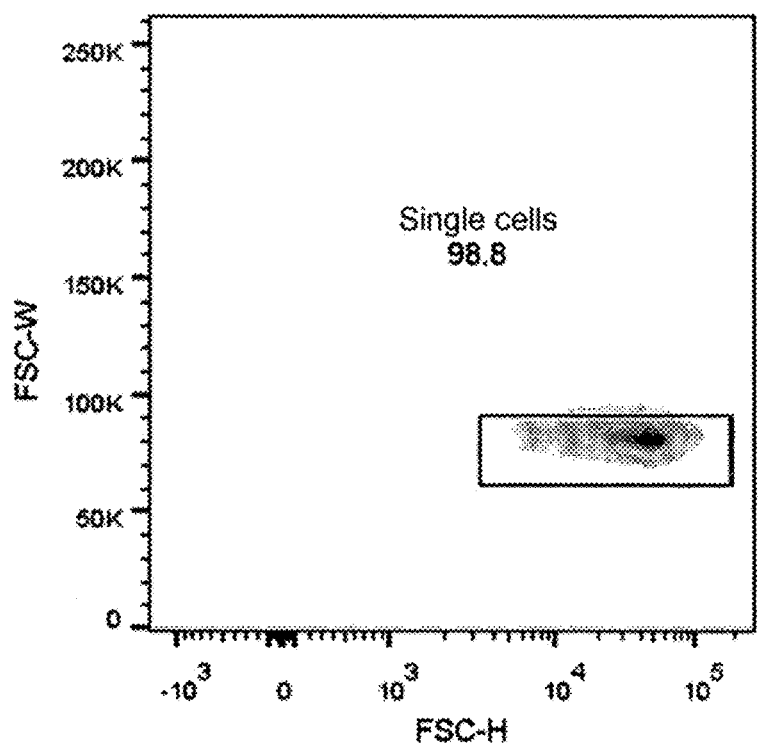

FIG. 2A: Cytogram showing the red blood cell populations. Along the abscissa: Log FSC-H (Forward Scatter-height). Along the ordinate: Log FSC-W (Forward Scatter-width).

Figure 2B:
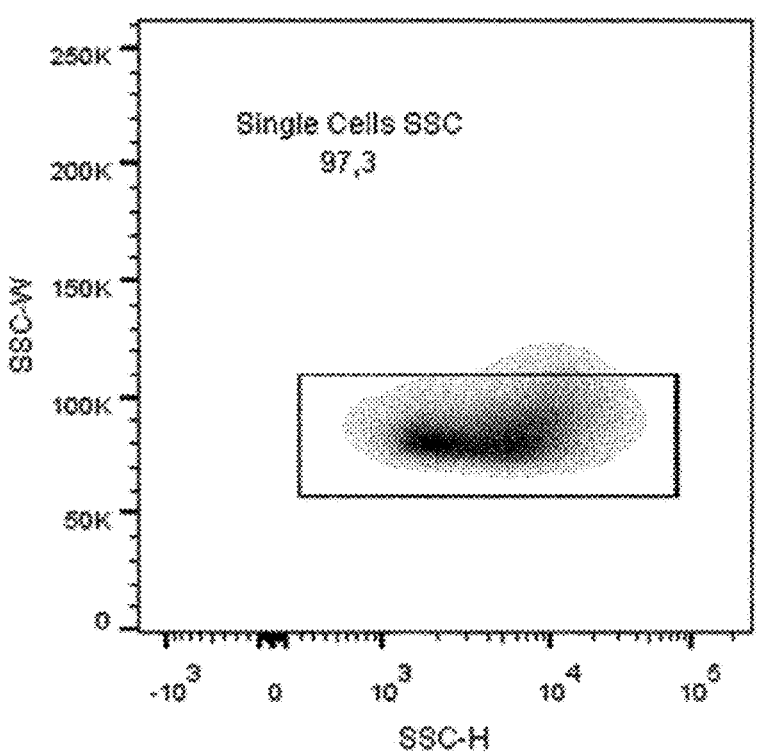

FIG. 2B: Cytogram showing the red blood cell populations. Along the abscissa: Log SSC-H (Side Scatter-height). Along the ordinate: Log SSC-W (Side Scatter-width).

The selection of the red blood cell singlets was carried out on the height and width parameters of the FSC signal first, then on the height and width parameters of the SSC signal.

Figure 3A:
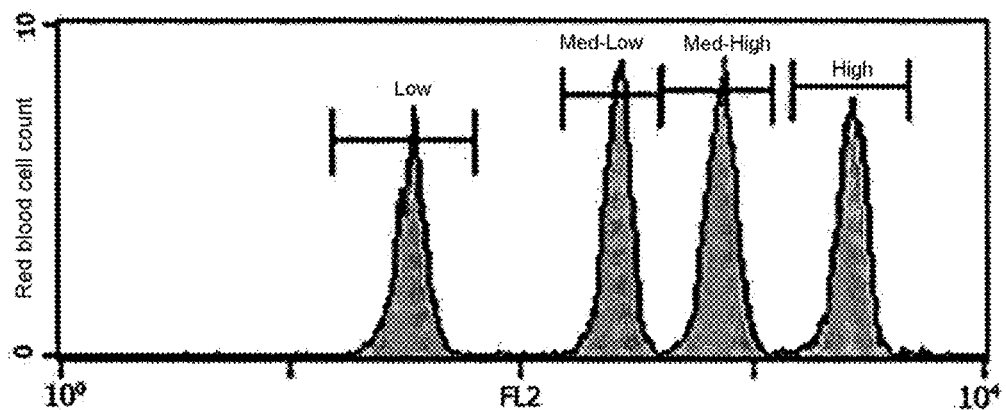

FIG. 3A: Cytogram showing the histograms of bead fluorescence distribution. Low: histogram of fluorescence distribution of the beads coupled with the lowest fluorochrome (PE) number. Med-Low: histogram of fluorescence distribution of the beads coupled with a medium-low fluorochrome (PE) number. Med-High: histogram of fluorescence distribution of the beads coupled with a medium-high fluorochrome (PE) number. High: histogram of fluorescence distribution of the beads coupled with a high fluorochrome (PE) number. Along the abscissa: Log FL-2 or PE-A indicating the fluorescence intensity for the Phycoerythrin fluorochrome. Along the ordinate: red blood cell count.

Figure 3B:
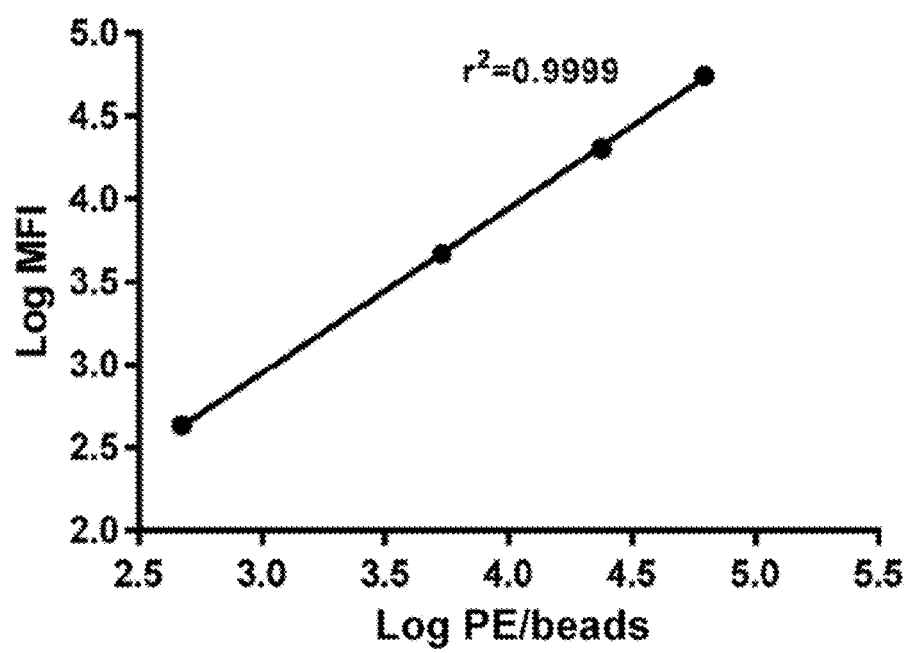

FIG. 3B: Linear regression straight line associating the fluorescence of the 4 populations of beads (Low, Med-Low, Med-High and High) and the fluorochrome (PE) number per bead. Along the abscissa: Log of the fluorochrome (PE) number per bead. Along the ordinate: Log bead fluorescence.

Figure 4C:
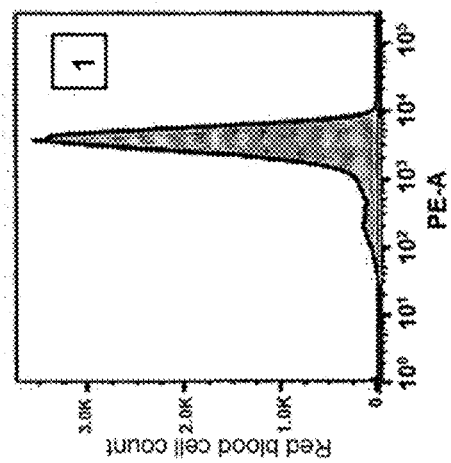
Figure 4F:
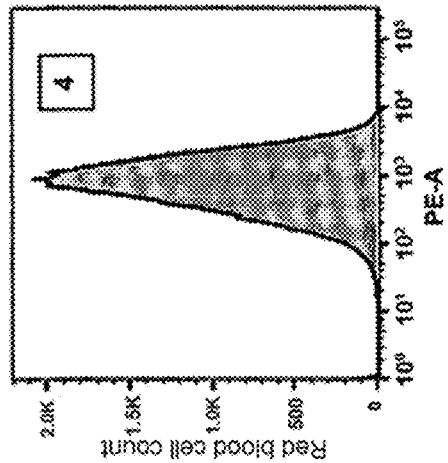
Figure 4B:
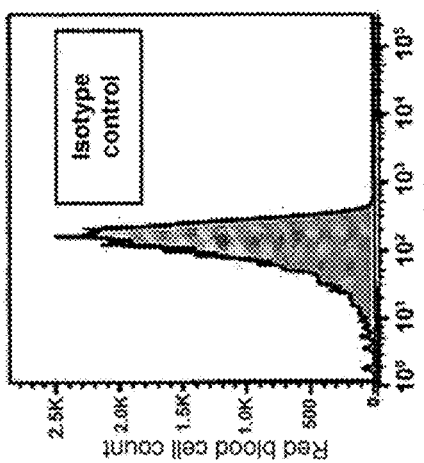
Figure 4E:
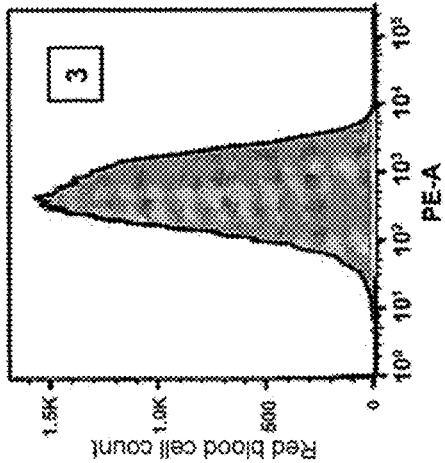
Figure 4A:
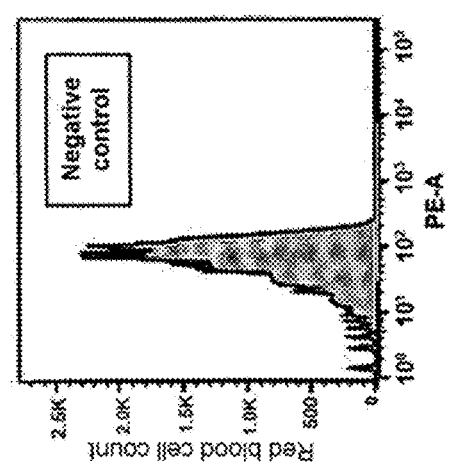
Figure 4D:
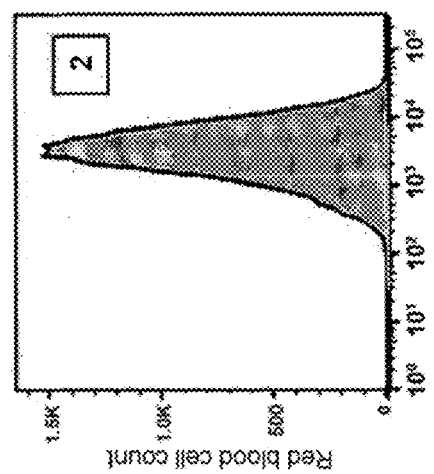
Figure 4G:
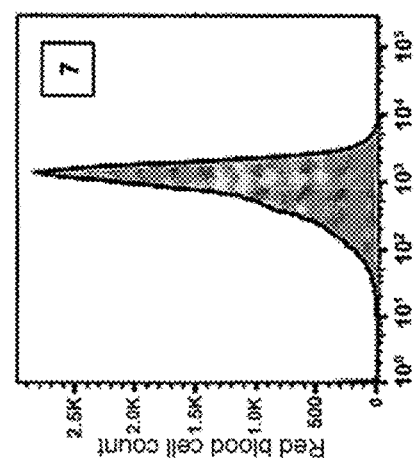
Figure 4H:
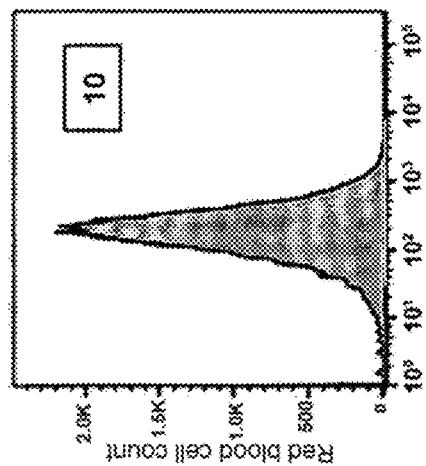
Figure 4I:
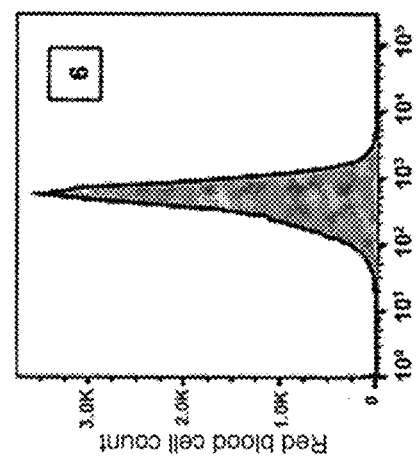
Figure 4J:
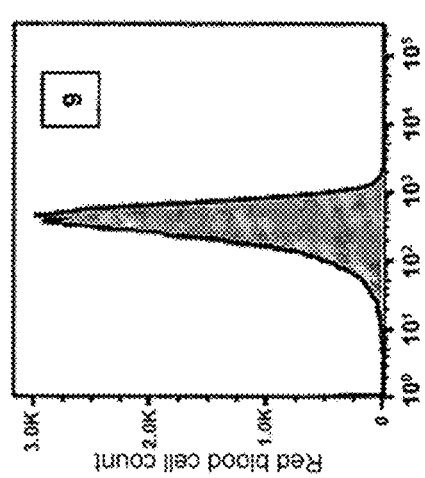
Figure 4K:
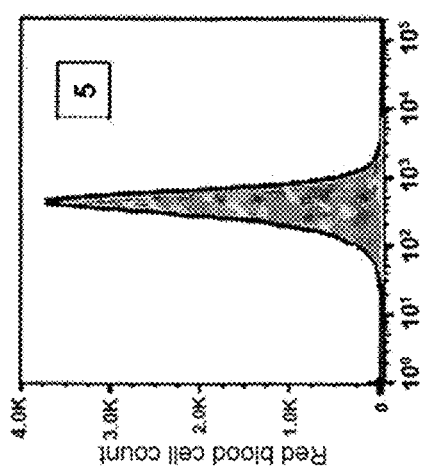
Figure 4L:
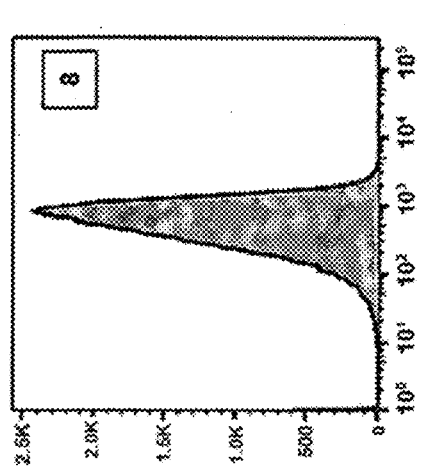

FIG. 4A: Cytograms showing the histogram of fluorescence distribution of the red blood cells for the negative control sample. Along the abscissa: Log PE-A indicating the fluorescence intensity for the Phycoerythrin fluorochrome. Along the ordinate: red blood cell count.

FIG. 4B: Cytogram showing the histogram of fluorescence distribution of the red blood cells for the isotype control sample. Along the abscissa: Log PE-A indicating the fluorescence intensity for the Phycoerythrin fluorochrome. Along the ordinate: red blood cell count.

FIGS. 4C, 4D, 4E, 4F, 4G, 4H, 4I, 4J, 4K, 4L, 4M, and 4N: Cytograms showing the histogram of fluorescence distribution of the red blood cells from samples of the patients 1 to 12 respectively. Along the abscissa: Log PE-A indicating the fluorescence intensity for the Phycoerythrin fluorochrome. Along the ordinate: red blood cell count.

Figure 5:
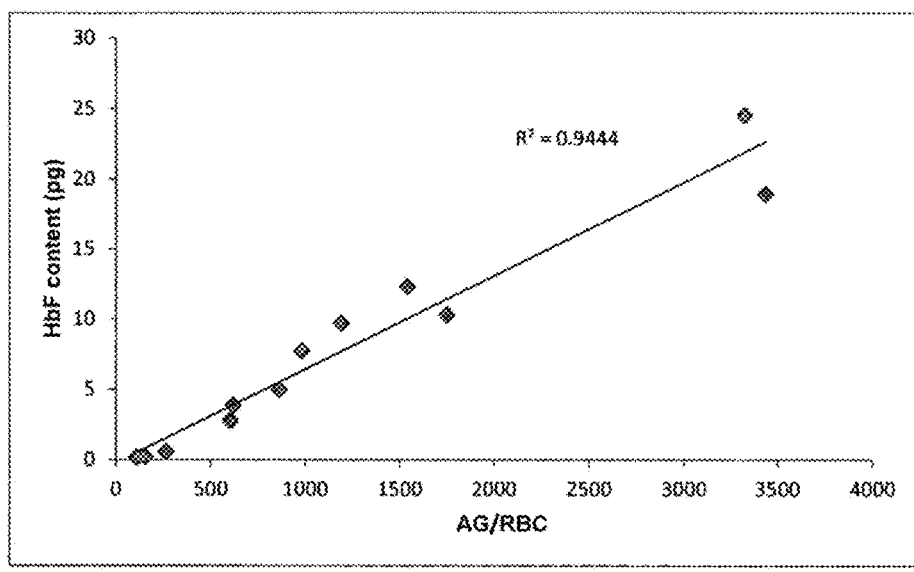
Figure 6H:
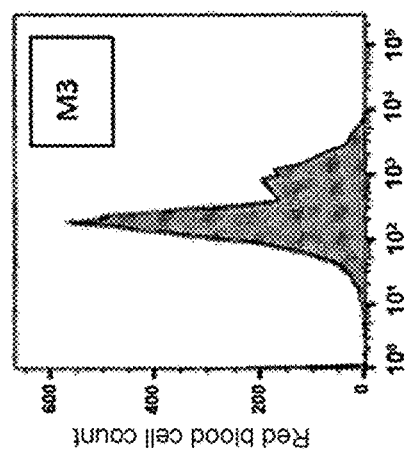
Figure 6I:
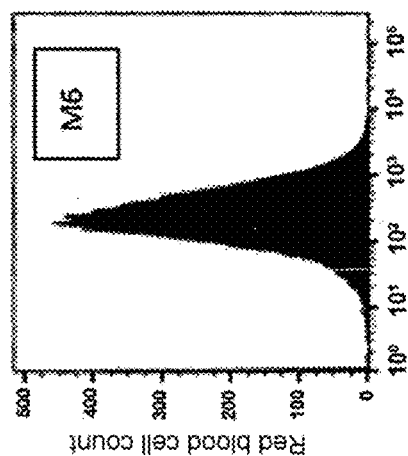
Figure 6J:
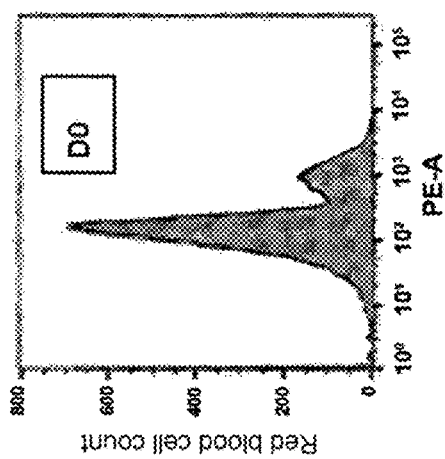
Figure 6K:
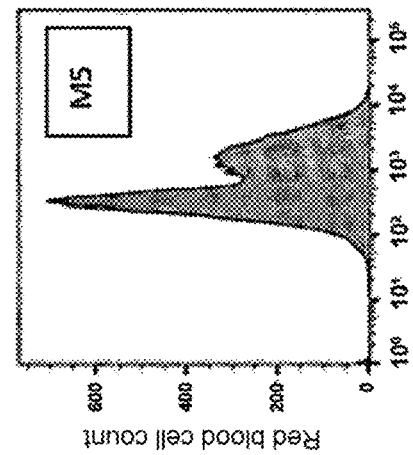

FIG. 5: Linear regression associating the HbF content (pg) and antigen amounts per red blood cell (AG/RBC). Along the abscissa: antigen amounts per red blood cell (AG/RBC). Along the ordinate: HbF content (pg).

FIGS. 6A, 6B, 6C, and 6D: Analysis of HbF distribution in patient A, before (D0) and during the treatment with hydroxyurea (M1, M4, M6). Along the abscissa: Log PE-A indicating the fluorescence intensity of the red blood cells for the Phycoerythrin fluorochrome. Along the ordinate: red blood cell count. The red blood cell samples were treated according to the same procedures as those carried out for the red blood cells of the patients serving as the HbF content range.

FIGS. 6E, 6F, and 6G: Analysis of HbF distribution in patient B before (D0) and during the treatment with hydroxyurea (M4, M9). Along the abscissa: Log PE-A indicating the fluorescence intensity of the red blood cells for the Phycoerythrin fluorochrome. Along the ordinate: red blood cell count. The red blood cell samples were treated according to the same procedures as those carried out for the red blood cells of the patients serving as the HbF content range.

FIGS. 6H, 6I, 6J, and 6K: Analysis of HbF distribution in patient C before (D0) and during the treatment with hydroxyurea (M3, M5, M6). Along the abscissa: Log PE-A indicating the fluorescence intensity of the red blood cells for the Phycoerythrin fluorochrome. Along the ordinate: red blood cell count. The red blood cell samples were treated according to the same procedures as those carried out for the red blood cells of the patients serving as the HbF content range.

Figure 7:
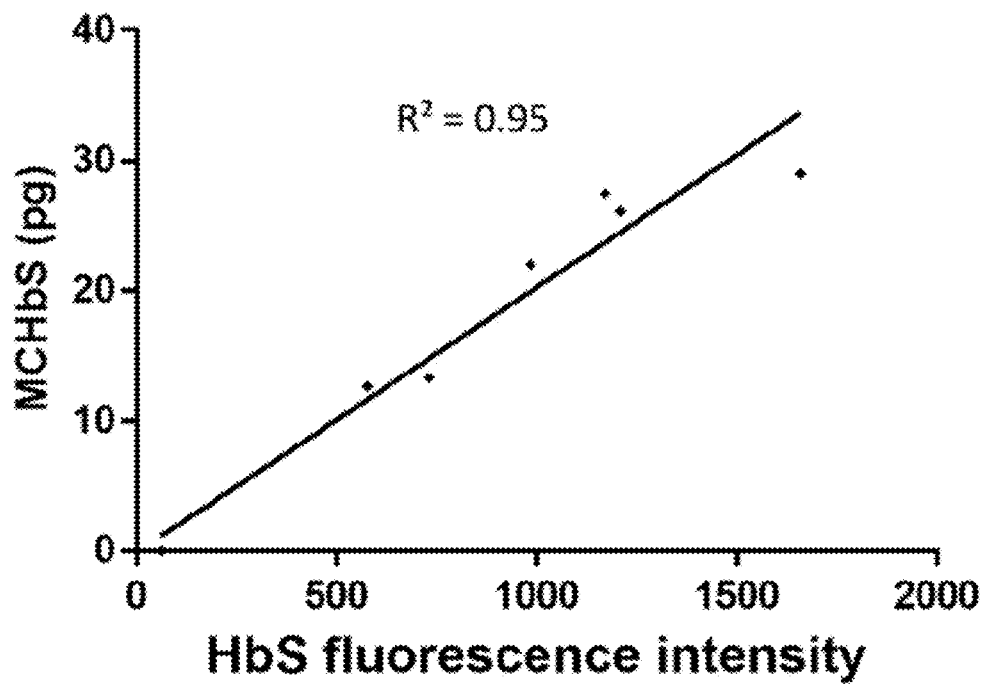

FIG. 7: Linear regression associating the HbS content (pg) to the measured fluorescence intensity. Along the abscissa: fluorescence intensity. Along the ordinate: HbS content (pg).

Figure 8:
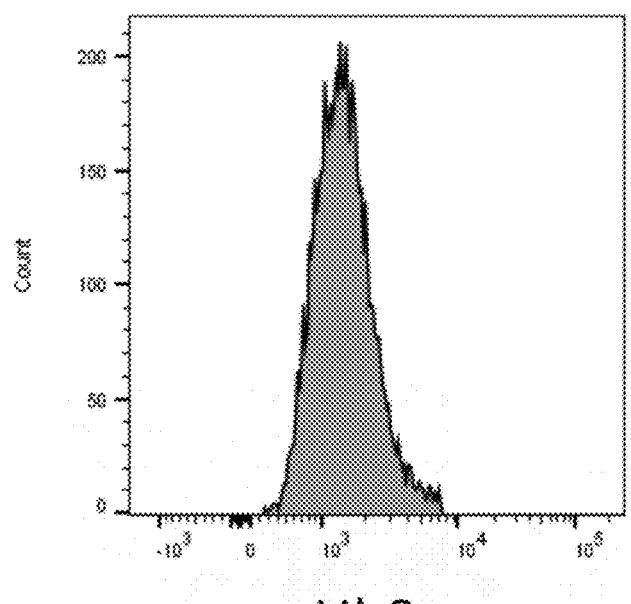

FIG. 8: Analysis of HbS distribution in patient 1 using the present method. Along the abscissa: the fluorescence intensity of the red blood cells for labelled HbS. Along the ordinate: red blood cell count. The red blood cell samples were treated according to the same procedures as those carried out for the red blood cells of the patients serving as the HbF content range.

Figure 9:
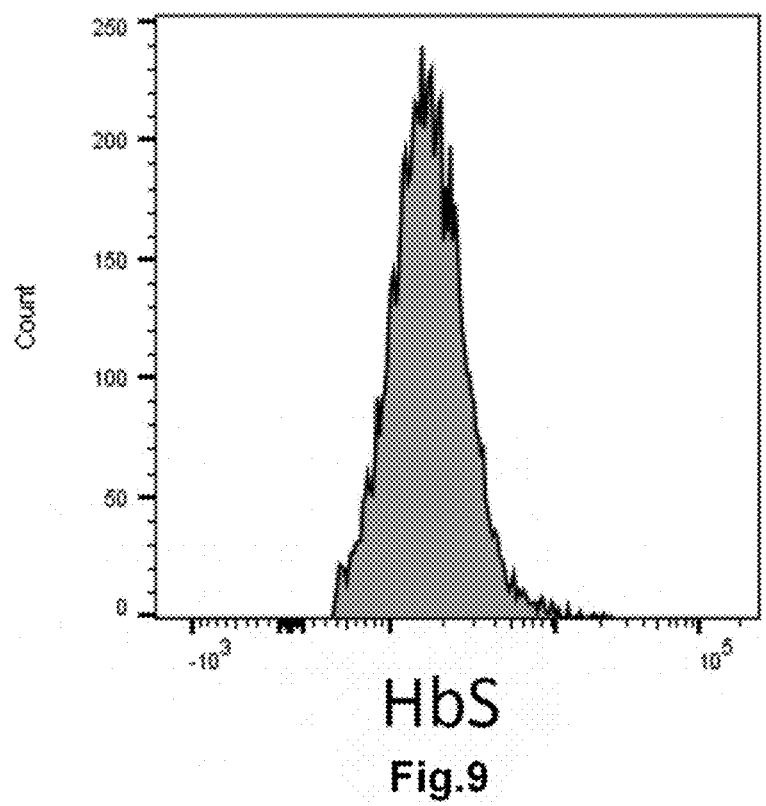

FIG. 9: Analysis of HbS distribution in patient 2 using the present method. Along the abscissa: the fluorescence intensity of the red blood cells for labelled HbS. Along the ordinate: red blood cell count. The red blood cell samples were treated according to the same procedures as those carried out for the red blood cells of the patients serving as the HbF content range.

Figure 10:
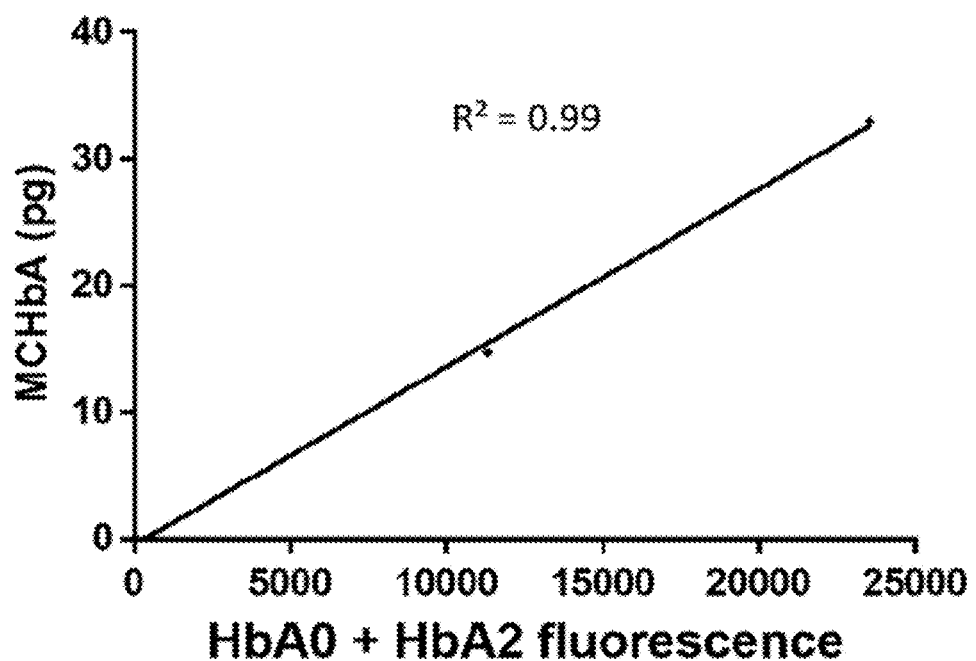

FIG. 10: Linear regression associating the HbA content (pg) to the measured fluorescence intensity. Along the abscissa: fluorescence intensity. Along the ordinate: HbA content (pg).

EXAMPLES

Example 1: Development of a Method for Determining the HbF Content of Each Red Blood Cell: Construction of a Standard Curve A group of patients having a perfectly homogeneous distribution of the HbF content of each red blood cell was selected from the SICLOPEDIE collection monitored at the Unite de Maladies Génétiques du Globule Rouge [Red Blood Cell Genetic Diseases Unit] at the Centre Hospitalier Universitaire Henri Mondor [Henri Mondor University Hospital Center] in Créteil. This group is composed of adult patients (age≥18 years old) having a hereditary persistence of HbF (HPFH) or intermediate or minor β-thalassemia, and an HbF content of each of their red blood cells which is homogeneous and constant over time. The HbF content of the total red blood cells of patients was determined, in the context of patient monitoring, by regular measurement of the % HbF (by HPLC) and of the mean HbF content per red blood cell (MCHbFCo). Patients having a major sickle cell syndrome (SS, SB-Thalassemia or SC) or a sickle cell trait (AS) and also patients treated with an HbF inducer (Hydroxyurea), patients having been transfused during the past 3 months before inclusion and pregnant patients were not included.

In accordance with the Declaration of Helsinki on the ethical principles applicable to medical research involving human beings (World Medical Association, text in force 2008, paragraph 24), all selected patients were informed of the risks and benefits of this study and provided written consent before inclusion. In accordance with the legislation in force (Articles L.1121-3 and R.5121-13 of the French Public Health Code), the information relating to the patients was protected anonymously in order to ensure confidentiality throughout the duration of the study.

This research protocol was approved by the International Review Board Ile-de-France IV located at the Hospital Saint-Louis (IRB No. 00003835).

In summary, 20 ml of blood were taken from the selected patients and collected in 5 tubes containing EDTA. The samples were treated within 24 h after having been taken: determination of the mean HbF concentration (using HPLC), blood hemogram, and flow cytometry analysis then freezing of the remaining samples at −80° C. for the subsequent analyses.

The detailed protocol is explained below.

1. Pre-Treatment of the Samples 20 ml of blood were taken from the selected patients and collected in 5 tubes containing EDTA. The red blood cells were recovered after fractionation of the whole blood by centrifugation at 800 G for 10 minutes at ambient temperature. Approximately 8 ml of blood cell pellet were collected and then washed in 10 ml of phosphate buffer (DPBS 1× Gibco by Life Technologies Cat 14190-094, Life Technologies SAS, Saint Aubin, France) in a 50 ml polypropylene tube. After homogenization, the blood cell suspensions were centrifuged at 1200 G for 5 minutes at ambient temperature. The blood cell pellet was recovered after elimination of the supernatant, and the washing procedure was carried out 3 times.

A first measurement of the HbF content (% HbF by HPLC×MCHCo) was carried out on approximately 1 ml of fresh sample, while 7 ml of blood cell pellet were stored at −80° C. in aliquot fractions of 200 µl in cryotubes (Nalgene Cat 479-6841) using glycerol (B Braun formula No. 569) as cryoprotective agent. For that, approximately 57.7% (V/V) of glycerol were added to the blood cell pellets in 2 steps. Specifically, in order to prevent precipitate formation, ⅓ of the glycerol volume was added dropwise to the blood cell pellet, in a first step, while agitating the cryotube, followed by an incubation for 10 minutes at ambient temperature, and the glycerol volume was subsequently made up with the remaining ⅔. With this procedure, the red blood cells can be stored for several months, or even years, while at the same time limiting lysis thereof.

The thawing consists of an incubation of the red blood cells in a bath at 37° C. or rapid agitation in the hand, followed by a series of washing using 2 solutions of NaCl in decreasing concentrations in order to remove the glycerol and to preserve the isotonicity. For that, 75 µl of deglycerolization solution (12% NaCl, B Braun formula No. 570 Melsungen, Germany) were added dropwise in a first step while homogenizing the blood cell suspensions, then the suspensions were incubated at ambient temperature for 10 minutes. Subsequently, 125 µl of NaCl at 0.9% containing glucose were added and the suspensions were incubated for 5 minutes at ambient temperature. Approximately 4×125 µl of NaCl at 0.9% containing glucose were added while observing an incubation of 5 minutes between each volume of NaCl at 0.9% containing glucose. The blood cell suspensions were transferred into 2 ml Eppendorf tubes, then fractionated by gentle centrifugation at 300 G for 10 minutes at ambient temperature while applying a deceleration equal to 5. After removal of the supernatant, 4×125 µl of NaCl at 0.9% containing glucose were added while observing an incubation of 5 minutes between each volume of NaCl at 0.9% containing glucose, then the suspensions were centrifuged as previously. In order to obtain a dry pellet of red blood cells, 500 µl of NaCl at 0.9% containing glucose were added in one step, followed by a centrifugation at 800 G for 10 minutes at ambient temperature. At the end of the final certification, the cell samples can be brought to the desired hematocrit by making up the volume with a buffer solution.

2. Determination of the HbF Content of Each Red Blood Cell

The determination of the HbF content of each red blood cell of the samples from selected patients was carried out both in the fresh cell samples and in the thawed samples using the following 3 methods:

high-performance liquid chromatography (HPLC) to determine the mean HbF percentage over all of the red blood cells blood hemogram (including the mean MCHCo); and flow cytometry.

2.1. Determination of the Mean HbF Percentage by HPLC

The determination of the mean HbF percentage by HPLC in the blood cell suspensions was carried out on a Variant II system (Cat: 2702000 Hemoglobin Testing System, Bio-Rad Laboratories, Marnes-la-Coquette, France). It is an ion exclusion liquid chromatography which makes it possible to separate 3 types of hemoglobins: HbF, HbA and HbA2 by virtue of the V2_B-THAL_DU method. The system is composed of a stationary phase composed of resin to which negatively charged carboxyl groups are attached and of a mobile phase composed of two Bis/Tris phosphate buffer solutions having a low and a high ionic strength respectively, and also of a photometric detector emitting 2 different wavelengths: 690 nm and 415 nm for detecting the negative control and the samples respectively. This system makes it possible to quantify the 3 hemoglobins from total blood or from a blood cell suspension with a minimum volume of 500 µl. For a sample of less than 500 µl, a dilution to 1:200 (v/v) with a dilution reagent was carried out before proceeding with the analysis. The analytes were separated as a function of their ionic interaction with the carboxyl groups over a total period of 6 minutes. The HbF was eluted after approximately 0.5 min. The data acquisition was carried out on a CDM 5.2 program in order to determine the mean percentages of each type of Hb. The mean HbF percentage is obtained according to the following relationship:

% HbF=(AUC HbF/AUC total Hb)×100 where % HbF represents the mean HbF percentage over all of the erythrocyte cells; AUC HbF represents the area under the curve of the HbF on the chromatogram; AUC total represents the sum of the areas under the curves of the 3 different types of Hb, corresponding in these patients to HbA, HbA2 and HbF.

2.2. Determination of the Mean Hemoglobin Content Per Red Blood Cell (MCHCo)

The mean hemoglobin content per red blood cell (or mean corpuscular hemoglobin content or MCHCo) constitutes a blood cell constant obtained by complete blood count or blood hemogram. The MCHCo is determined by calculation, by dividing the hemoglobin concentration expressed per liter of blood by the number of red blood cells per liter of blood.

This analysis was carried out on a Horiba ABX Micros ES 60 automated counter (HORIBA Medical, Montpellier, France) on a minimum volume of sample of 500 µl having a hematocrit at approximately 50%.

2.3. Determination of the Mean HbF Content Per Red Blood Cell (MCHbFCo)

The determination of 2 mean parameters (% HbF and MCHCo) obtained by HPLC and by blood hemogram made it possible to calculate the mean HbF content per red blood cell, or MCHbFCo, according to the following relationship: MCHbFCo=(% HbF×MCHCo)/100 where MCHbFCo (pg) represents the mean HbF content per red blood cell;

% HbF represents the mean HbF percentage determined by HPLC (see 2.1);

MCHCo represents the mean Hb content per red blood cell provided by the automated counter (see 2.2).

3. Determination of the Fluorescence of the Red Blood Cells Labeled with an Anti-HbF Antibody by Flow Cytometry 3.1. Instruments The analysis of the HbF content of each red blood cell was carried out on an 8-color BD FACS Canto II cytometer (Cat 338960, BD Biosciences, Le Pont de Claix, France) combined with the DIVA® data acquisition software.

Flow cytometry or FACS (fluorescence-activated cell sorting) is a technique which makes it possible to individually analyze the properties (size, granulosity and fluorescence) of particles (beads or cells) in suspension in a flow system.

It is an immunological method based on the immunophenotyping technique which consists of an antigenic detection by virtue of recognition by a specific antibody which is usually conjugated to a fluorescent molecule. The signal measured is principally the fluorescence intensity, which is proportional to the amount of antigens detected by the specific antibody. The cytometry data acquisition requires pre-processing of the samples, which consists in fixing and permeabilizing the cell membrane, followed by intracellular labeling with an HbF-specific antibody conjugated to a fluorochrome.

3.2. Fixing and Permeablilizing of the Red Blood Cell Membrane

The fixing and permeabilizing of the RBC membrane was carried out using the reagents of a kit for detecting F cells called "Fetal Cell Count™ kit" (Cat IQP-349, IQ Products, Groningen, the Netherlands).

In order to fix the blood cell membrane, 5 µl of washed blood blood cell pellet (fresh or frozen) were added and homogenized in 100 µl of fixing reagent or reagent A containing a preservative or sodium azide (Fetal Cell Count™ kit, Cat IQP-349). 100 µl of buffered formaldehyde solution or fixing solution B (Fetal Cell Count™ kit, Cat IQP-349) were subsequently added to the blood cell suspension. The suspension was homogenized by vortexing and then incubated at ambient temperature for exactly 30 minutes. The blood cell suspension was carefully homogenized every 10 minutes. The RBCs were subsequently washed in 2 ml of 1×PBS buffer containing heparin (reagent D Fetal Cell Count$^7$M kit, Cat IQP-349), followed by centrifugation at 300 G for 3 minutes at ambient temperature. The washed blood cell pellet was resuspended by adding 100 µl of 1×PBS buffer (reagent D Fetal Cell Count™ kit, Cat IQP-349).

In order to permeabilize the blood cell membrane, 100 µl of sodium dodecyl sulfate solution, permeabilization reagent (reagent C Fetal Cell Count™ kit, Cat IQP-349) were added to the suspension of fixed RBCs. The samples were incubated for exactly 3 minutes at ambient temperature. The RBCs were washed as previously. The wash was carried out twice. After removal of the supernatant, the blood cell pellets were resuspended in 1 ml of 1×PBS buffer (reagent D Fetal Cell Count™ kit, Cat IQP-349).

3.3. Intracellular Labeling of the Fixed and Permeabilized Red Blood Cells

An IgG1 Kappa clone mouse monoclonal antibody directed specifically against the gamma chain of human HbF and conjugated with phycoerythrin (PE) (reagent F Fetal Cell Count™ kit, Cat IQP-349, IQ Products) was used to determine the HbF content of each previously fixed and permeabilized red blood cell. For that, 50 µl of antibody solution were deposited in 50 µl of suspension obtained in 3.2. Phycoerythrin, by virtue of its conformational (steric hindrance) properties has the advantage of having a PE:antibody ratio close to 1.

A sample not labeled with the antibody was used as a negative control, while an isotype control was prepared by adding 20 µl of PE-coupled mouse IgG1 Kappa (Cat: 555749, BD Pharmingen™, Le Pont De Claix, France) in 50 µl of suspension obtained in 3.2 in order to verify the binding specificity of the anti-HbF antibody used.

The labeled and nonlabeled samples and also the isotype control were incubated for 15 minutes in the dark and at ambient temperature. The RBCs were subsequently washed in 2 ml of 1×PBS buffer (reagent D Fetal Cell Count™ kit, Cat IQP-349), followed by centrifugation at 300 G for 3 minutes at ambient temperature. The washed blood cell pellets while resuspended by adding 500 µl of 1×PBS buffer (reagent D Fetal Cell Count™ kit, Cat IQP-349). The red blood cells were analyzed in the cytometer within minutes following their pre-processing.

3.4. Cytometer Sample Analysis

During the analysis, the samples were placed in a cold (ice) chamber and in the dark in order to prevent fluorescence losses. Before the data acquisition, the cytometer is precalibrated according to the supplier's recommendations.

Figure 1A:
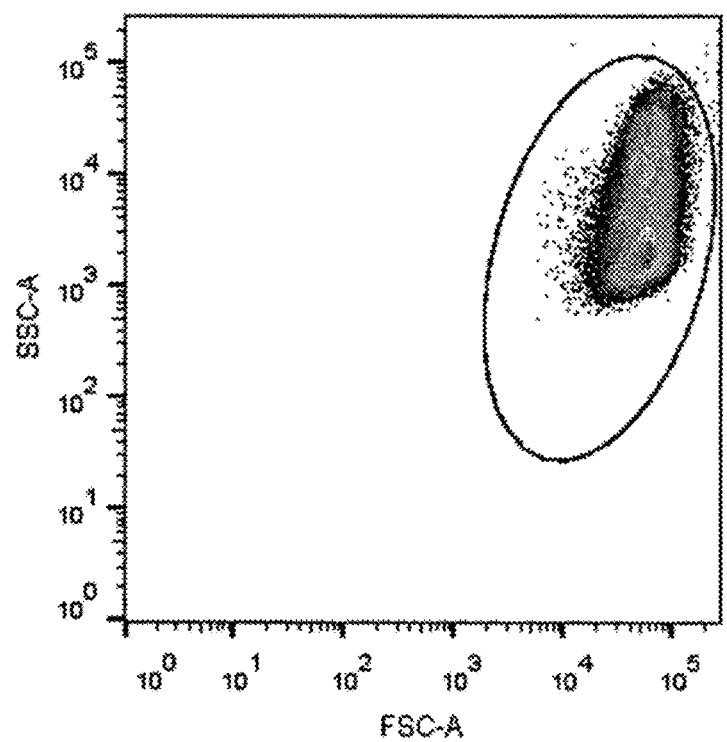
FIG. 1A: Cytogram showing the red blood cell populations. Along the abscissa: Log FSC (Forward Scatter) indicating the morphology of the cells. Along the ordinate: Log SSC (Side Scatter) indicating the granulosity of the cells. The selection of the blood cells was carried out on a logarithmic scale for the gains of the FSC and SSC parameters and on a negative control sample.
Figure 1B:
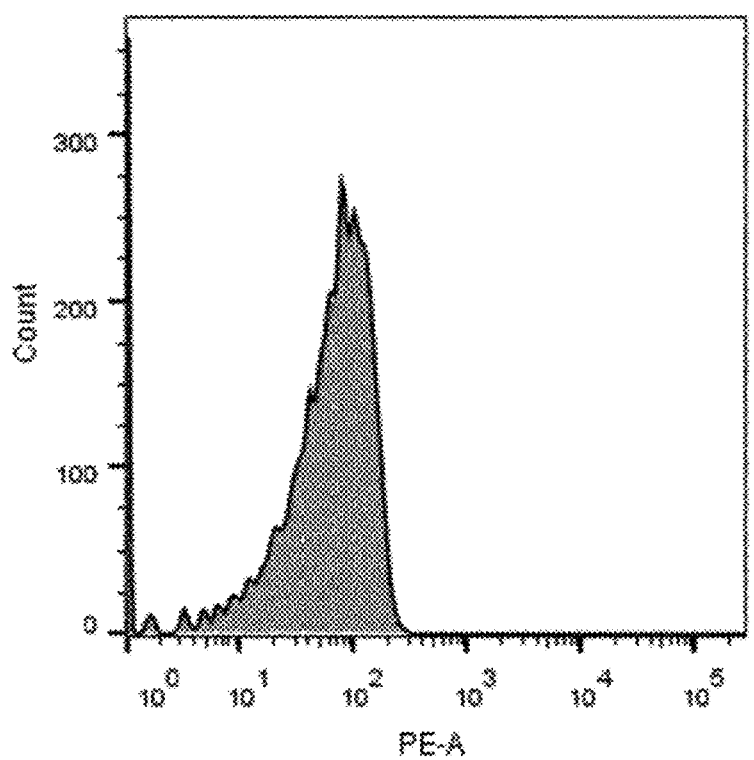
FIG. 1B: Cytogram showing the histogram of red blood cell fluorescence distribution. Along the abscissa: Log PE-A indicating the fluorescence intensity for the Phycoerythrin fluorochrome.

The nonlabeled sample was used to determine the voltages (or PMT) of each parameter: FSC (Forward Scatter), SSC (Side Scatter) and fluorescence (table 1). The selection of the red blood cell populations was based on the criteria of size or FSC and granulosity or SSC on the Log FSC-A vs Log SSC-A cytogram while eliminating the debris and background noises. The negative control was determined on the signal generated by the sample not labeled by fluorescence (FIG. 1A). Logarithmic scales were preferred for the FSC and SSC gains.

TABLE 1

Adjustment of the cytometer obtained with the sample of nonlabeled red blood cells

| Parameter | Voltage | Log | A | H | W |
|---|---|---|---|---|---|
| FSC | 341 | ✓ | ✓ | ✓ | ✓ |
| SSC | 328 | ✓ | ✓ | ✓ | ✓ |
| PE | 400 | ✓ | ✓ | ✓ | ✓ |

The exclusion of the red blood cell (RBC) doublets was carried out with a low flow rate by selecting the RBC populations on the FSC-W vs FSC-H then SSC-W vs FSC-H cytograms according to FIG. 2A and FIG. 2B.

A minimum number of 100 000 RBC events were collected in order to improve the accuracy of the analysis and to register a sufficient number of RBCs after the exclusion of the doublets. For each sample, the statistics were generated by the acquisition software (Diva®) with the number of events recorded for each RBC population selected. The fluorescence intensity (MFI) is given as geometric mean and arithmetic mean.

4. Determination of the Amount of Labeled HbF Antigen Concentration Per Red Blood Cell or AG/RBC In order to determine the amount of labeled HbF per red blood cell, the fluorescence intensity obtained with the flow cytometer was converted into amount of labeled HbF per red blood cell (AG/RBC) by means of the calibrated beads contained in a phycoerythrin fluorescence quantification kit (Becton Dickinson QuantiBRITE PE, Cat: 340495, BD Biosciences, Le Pont De Claix, France). These beads are conjugated to phycoerythrin in such ways to provide 4 levels of fluorescence (Low, Medlow, MedHigh and High) corresponding to a number of phycoerythrin molecules per bead (FIG. 3A). Before the fluorescence data acquisition in the cytometer, the beads were reconstituted in 500 µl of labeling buffer solution composed of 1×PBS/0.02% NaN$_3$ (v/v) (Cat: 296028 ChemCruz™ Biochemicals, Santa Cruz Biotechnology, Germany) supplemented with 1% of BSA (Cat: A3803, Sigma, Saint-Quentin Fallavier France). A minimum of 10 000 beads were collected with the same adjustments used for the samples analyzed in point 3.4. The data acquired in the cytometer made it possible to plot a calibration straight line associating Log fluorescence (Log MFI) and Log PE/bead (FIG. 3B). By applying the latter to the fluorescence of the RBCs labeled with the anti-HbF antibody, it is possible to deduce the amount of fluorescent molecules per red blood cell. By using the PE:antibody ratio, the number of fluorescent molecules per red blood cell can be converted into number of antibodies bound per red blood cell, that is to say into number of molecules of antigen (i.e. HbF) per red blood cell (AG/RBC).

5. Determination of the HbF Content (Pq) of Each RBC on the Basis of AG/RBC and the MCHbFCo The data recorded by the acquisition software of the flow cytometer (Diva®) were processed on FlowJo V10 (Cat 130-099-429 Miltenyi Biotec, Paris, France). This is a program for analysis and visualization of the cytometry data exported in "flow cytometry standard" or fcs format. The FlowJo software made it possible to generate the values of each parameter (FSC, SSC, Fluorescence) for each event.

For each RBC sample collected for this study, the distribution of HbF labeled with the antibody is represented by a histogram associating the number of red blood cells and the Log of fluorescence.

The mean HbF content per red blood cell (MCHbFCo) of each sample of selected patients, obtained by the combination of HPLC and of MCHCo, was associated with the mean fluorescence converted into AG/RBC by virtue of the quantification beads.

In order to determine the HbF content (in pg) of each red blood cell, a standard curve was constructed on the basis of the MCHbFCo values and the AG/RBC values, thus giving a range of known MCHbFCo values associated with the fluorescence (FIG. 5).

Example 2: Validation of the Method for Determining the HbF Content of Each Red Blood Cell

1. Characteristics of the Included Patients

A cohort of 12 patients was selected in order to constitute a range of HbF content, the criterion for selecting these patients was the confirmation of a homogeneous distribution, Log-Normal of their HbF. The data from these patients were used to construct a standard curve (cf. example 1, point 5) serving to determine the HbF content of each red blood cell. Table 2 summarizes the demographic data and the genetic characteristics of these patients.

TABLE 2

Demographic and biological data of the included patients for constructing the standard curve

| Patients | Age at inclusion (years) | Sex | Genetic characteristics | HbF (%) | MCHCo (pg) | MCHbFCo (pg) | MCV (µm$^3$) |
|---|---|---|---|---|---|---|---|
| 1 | 18 | Male | β-thalassemia | 100 | 24.5 | 24.5 | 73 |
| 2 | 62 | Male | β-thalassemia | 69.6 | 27.2 | 18.93 | 91 |
| 3 | 50 | Male | β-thalassemia | 61.5 | 20.1 | 12.36 | 64 |
| 4 | 46 | Male | β-thalassemia | 53.2 | 19.3 | 10.27 | 63 |
| 5 | 50 | Female | Ghanaian HPFH2 | 34.80 | 28 | 9.74 | 81 |
| 6 | 39 | Female | β-thalassemia | 27.9 | 28 | 7.76 | 81 |

TABLE 2-continued

Demographic and biological data of the included patients for constructing the standard curve

| Patients | Age at inclusion (years) | Sex | Genetic characteristics | HbF (%) | MCHCo (pg) | MCHbFCo (pg) | MCV (μm³) |
|---|---|---|---|---|---|---|---|
| 7 | 39 | Male | β-thalassemia | 21 | 23.8 | 5 | 72 |
| 8 | 43 | Female | β-thalassemia | 16.4 | 23.6 | 3.87 | 71 |
| 9 | 37 | Male | β-thalassemia | 14.9 | 18.5 | 2.76 | 62 |
| 10 | 60 | Female | β-thalassemia | 2.7 | 23.4 | 3.11 | 67 |
| 11 | 58 | Male | β-thalassemia | 0.8 | 19.4 | 0.15 | 64 |
| 12 | 23 | Male | β-thalassemia | 0.8 | 27.8 | 0.22 | 83 |

Figure 4N:
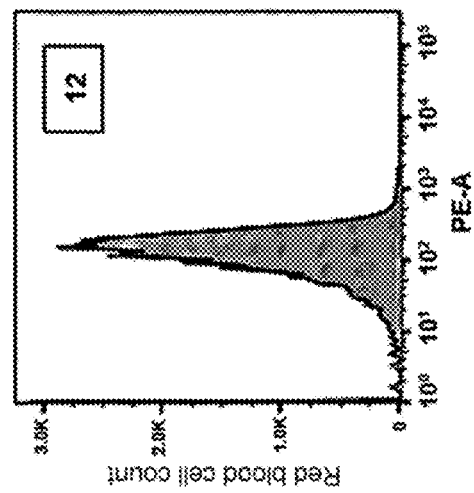
Figure 4M:
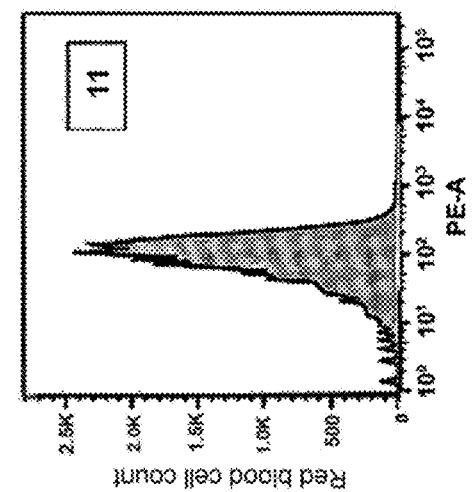

A homogeneous distribution of the red blood cell fluorescences and therefore of the HbF content was verified on the set of samples collected (FIG. 4A to FIG. 4N). FIGS. 4C to 4N shows, on a semi-logarithmic scale, the Log-normal distribution of the HbF content per RBC of the 12 patients of the range.

2. Test for Reproducibility of the Various Measurements

A reproducibility study was carried out by testing the variabilities on the following measurements:
MCHbFCo on fresh red blood cells and on red blood cells after a thawing series
MFI values obtained with the QuantiBRITE PE beads and the RBCs
AG/RBC after a thawing series No significant difference was observed on the MCHbFCo values (pg) obtained on fresh red blood cells and after 12 rounds of thawing (n=13, p>0.9999) or on the AG/RBC values measured after 11 rounds of thawing (p=0.73). Likewise, the analysis of variability of the data obtained on the quantification beads revealed no significant difference (n=11, p=0.99).

3. Method for Measuring the HbF Content in Each Red Blood Cell

The MCHbFCo range obtained in the patients having a homogeneous distribution of the HbF contents per red blood cell was associated with the fluorescence intensities and then with the amounts of antigens per red blood cell by means of the calibration beads. A standard curve (or regression straight line) was determined from the AG/RBC means obtained after 11 rounds of thawing and the MCHbFCo values of each patient (FIG. 5).

A coefficient of correlation at 97.18% ($r^2$=0.9444) was obtained between the MCHbFCo values and the means of the amounts of HbF antigen (labeled by the fluorescent antibody) per red blood cell, for the various patients. This standard curve makes it possible to determine the HbF content per RBC for a given fluorescence value. The accuracy of the measurements is given by a confidence interval at 95% determined from the "mean" standard curve, from the standard deviations between each regression and from the number of the regression model having served to calculate the mean.

Example 3: Study of the HbF Distribution During the Treatment with Hydroxyurea 1. Patients A monocentric, longitudinal, prospective study was carried out on a cohort of 29 adult sickle cell disease patients (age 18 years old) exhibiting an SS homozygotes mutation, beginning a treatment with hydroxyurea, regularly monitored at the major sickle cell syndrome reference Center at the Centre Hospitalier Universitaire Henri Mondor [Henri Mondor University Hospital Center] in Créteil. Patients having had an attack requiring hospitalization and/or a transfusion exchange program during the previous 3 months before inclusion and also patients who were pregnant or who were wanting to get pregnant were excluded from the study.

The patients exhibiting the eligibility criteria were monitored at various times before and during the treatment with hydroxyurea: D0 (before the beginning of the treatment with hydroxyurea), at 15 days, 1 month, 3 months, 4 months and 6 months or more after the setting up of the treatment with hydroxyurea (D15, M1, M3, M4 and ≥M6 respectively).

In accordance with the Declaration of Helsinki on the ethical principles applicable to medical research involving human beings (World Medical Association, text in force 2008, paragraph 24), all recruited patients were informed of the risks and benefits of this study and provided written consent before inclusion. In accordance with the legislation in force (Articles L.1121-3 and R.5121-13 of the French Public Health Code), the information relating to the patients was protected anonymously in order to ensure confidentiality throughout the duration of the study.

This research protocol was approved by the International Review Board Ile-de-France IV located at the Hospital Saint-Louis (IRB No. 00003835).

2. Methods

During each visit to the center (D0, D15, M1, M3, M4 and ≥M6), approximately 16 ml of blood were taken and collected in 4 tubes containing EDTA.

2.1. Pretreatment of the Blood Cell Samples

The samples were treated within 24 h of being taken. The treatment involves the separation of the red blood cells as a function of their density and the cryopreservation of the blood cell fractions and of the total or non-fractionated red blood cells.

3. Analysis of the Blood Cell Samples

The various measurements carried out on each blood cell fraction or on the total RBCs were composed of:
complete blood count or blood hemogram by an automated counter;
measurement of the mean HbF percentage (% HbF) by HPLC; and
flow cytometry measurement of the fluorescence intensity of each RBC labeled with an antibody directed against HbF in accordance with the protocol detailed in example 1.

3.1. Complete Blood Count, Measurement of the Mean HbF Percentage (% HbF) by HPLC These analyses were carried out on fresh RBCs and RBCs after thawing according to the same techniques as those described in example 1.

3.2. Measurement of the HbF Content of Each RBC by Flow Cytometry

This analysis was carried out after thawing of the RBCs stored at −80° C. according to the technique described in example 1.

The HbF content of each RBC was determined using the standard curve described in example 1 based on the fluorescence intensities of each red blood cell, converted into AG/RBC, using the QuantiBRITE PE beads. The measurements were carried out at each stage of the treatment (D0, D15, M1, M3, M4 and ≥M6) in the various blood cell fractions: non-dense, dense and total red blood cells.

4. Statistical Analyses

In the SS patients taking hydroxyurea, the percentages of RBCs containing HbF contents grouped together in arbitrarily defined categories (0 to 2 pg, 2 to 4 pg, 4 to 6 pg, etc.) were compared during the longitudinal monitoring in order to determine the variations in the HbF distribution before and during the treatment with hydroxyurea. The comparisons between each stage of the treatment were carried out by means of an ANOVA measurement repeated between D0, D15-M3 and M6 in the total red blood cells.

The statistical analyses were carried out using the GraphPad Prism® Version 6 software (RITME Informatique Paris France).

5. Results 5.1. Demographic Data and Indications of Hydroxyurea

In total, 29 adult SS patients were included. Out of the entire cohort, 10 patients were monitored between D0 and ≥M6, the RBC samples of a patient were hemolyzed, 9 patients were analyzed.

The demographic data of the included patients are summarized in table 3

TABLE 3

Demographic data of SS patients taking hydroxyurea

| | Men | Women |
|---|---|---|
| N | 13 | 16 |
| Age | 33 [28.50; 45] | 36 [31; 44.25] |

Age expressed as Median [25th percentile; 75th percentile]

The hydroxyurea was administered with an average dose of 15 mg/Kg/day for the following indications: VOC prevention, chronic visceral attacks, leg ulcers, sickle cell nephropathy, significant hemolysis with anemia, priapism, stroke 5.2. Biological Data The mean HbF percentage (% HbF) increases by approximately 3-fold after 6 months of treatment with hydroxyurea. The data are presented in table 4.

TABLE 4

Variation in %/HbF during the treatment with hydroxyurea

| | D0 | D15-M1 | M3-M4 | M6 | p (D0 and M6) |
|---|---|---|---|---|---|
| Total red blood cells | 2.65 [1.8-6.35] | 4.9 [1.85-8.4] | 7 [2.4-17.80] | 10.05 [3.33-19.13] | 0.03 |

Data expressed as Median [25th percentile; 75th percentile]

A significant increase in the mean corpuscular volume (MCV) and in the mean hemoglobin content per red blood cell (MCHCo) was observed after 6 months of treatment with hydroxyurea, indicating good patient conformity and the efficacy of the treatment despite the low patient numbers. The percentage of dense red blood cells has a tendency to decrease; however, this decrease is not significant. Likewise, for the mean corpuscular hemoglobin concentration (MCHC), the leukocytes and the platelets, no significant variation was observed. The results are presented in table 5.

TABLE 5

Biological data before and during the treatment with hydroxyurea

| | D0 | M6 | p |
|---|---|---|---|
| Hemoglobin (g/dl) | 8 [6.65-9.05] | 9.35 [7.30-10.10] | 0.2 |
| Leukocytes (Giga/l) | 10.70 [9.45-12.20] | 9 [5.35-11.58] | 0.11 |
| MCV (femtoliter) | 87 [83-95] | 100.50 [87.75-115] | 0.03 |
| MCHC (g/dl) | 32.60 [32.05-35.10] | 34.40 [32.43-35.70] | 0.08 |
| MCHCo (pg) | 29.70 [25.30-32.85] | 33.80 [30.70-39.65] | 0.008 |
| Platelets (giga/l) | 359 [288-548] | 318 [257-438.80] | 0.18 |

Data expressed as Median [25th percentile; 75th percentile]

5.3. HbF Distribution During the Treatment with Hydroxyurea

The qualitative analysis by flow cytometry of the response to treatment with hydroxyurea shows a heterogeneous HbF distribution before the beginning of the treatment in 8 patients. After 6 months of treatment with hydroxyurea, the HbF follows a homogeneous distribution in 6 patients. The HbF distribution becomes homogeneous starting from M2 in 1 patient and after ≥M4 in 5 patients. FIGS. 6A to 6K illustrates the variations in HbF distribution during the treatment with hydroxyurea in the total red blood cells.

The HbF distribution was quantitatively analyzed by means of the method described in study 1. The number and percentage of red blood cells per HbF content range (pg) was determined for each patient. The analysis of the red blood cell distribution over time while taking hydroxyurea was carried out in 9 patients. The results show a significant variation in the red blood cells having the lowest HbF contents (0 and 2 pg) with an increase of approximately 25% between D0 and M6. The red blood cells which have an HbF content of greater than 20 g increase significantly, by up to 3 times, after 6 months of treatment with hydroxyurea; however, this variation is not significant. The red blood cells which have medium-high contents exhibit much lower variations.

TABLE 6

Red blood cell distribution per HbF content range under hydroxyurea treatment

| HbF (pg) | D0 (% RBCs) | D15-M3 (% RBCs) | ≥M6 (% RBCs) | p |
|---|---|---|---|---|
| [0; 2[ | 71.13 (23.16 | 65.63 (25.13 | 53.17 (30.63 | 0.0083 |
| [2; 4[ | 9.14 (7.44 | 11.32 (6.80 | 15.05 (10.11 | 0.1868 |
| [4; 6[ | 4.54 (3.86 | 4.88 (2.90 | 6.70 (4.39 | 0.2226 |
| [6; 8[ | 3.16 (2.92 | 3.42 (2.52 | 3.92 (2.44 | 0.5186 |
| [8; 10[ | 2.42 (2.32 | 2.65 (2.18 | 2.72 (1.83 | 0.6932 |
| [10; 15[ | 1.94 (1.84 | 2.41 (2.73 | 2.55 (2.57 | 0.3926 |
| [15; 20[ | 3.66 (3.35 | 4.42 (4.27 | 4.29 (3.42 | 0.474 |
| ≥20 | 4.01 (4.35 | 5.27 (8.56 | 11.60 (18.64 | 0.1626 |

The data are expressed as mean (standard deviation)

The measurement of the fluorescence intensities of each red blood cell by flow cytometry made it possible to categorize each red blood cell as a function of the HbF content thereof. The analysis of the red blood cell distribution as a function of the HbF content thereof makes it possible to identify various treatment response profiles. By way of example, patients 11 and 24 (tables 7 and 8), expressing identical % HbF values at D0 (6%) and M6 (18%) with an MCHCo at D0=33.6 and 34.5 pg and at M6=38.9 and 42 pg (patients 11 and 24 respectively), exhibit 2 different distributions. In patient 11, a lower number of red blood cells is noted with an HbF content of less than 2 pg with a decrease of approximately 73% at M6, whereas patient 24 exhibits a higher number of red blood cells with an HbF content of less than 2 pg with a decrease of approximately 40% at M6. The HbF distribution in patient 11 is described by a bimodal curve at D0 and at M6, whereas the distribution of patient 24 exhibits a relatively homogeneous distribution over the low HbF amounts with a clear shift of the set toward higher amounts.

Patient 11

| HbF (pg) | D0 (% RBCs) | D15-M1 (% RBCs) | M3-M4 (% RBCs) | ≥M6 (% RBCs) |
|---|---|---|---|---|
| [0; 2[ | 48.44 | 55.38 | 48.83 | 12.93 |
| [2; 4[ | 26.27 | 23.31 | 31.73 | 17.62 |
| [4; 6[ | 8.13 | 6.25 | 9.30 | 11.85 |
| [6; 8[ | 3.77 | 3.07 | 4.32 | 8.05 |
| [8; 10[ | 2.69 | 2.55 | 2.04 | 6.08 |
| [10; 15[ | 2.41 | 2.24 | 0.72 | 6.13 |
| [15; 20[ | 4.21 | 4.42 | 2.46 | 9.77 |
| ≥20 | 4.08 | 2.78 | 0.59 | 27.57 |

Patient 24

| HbF (pg) | D0 (% RBCs) | D15-M1 (% RBCs) | M3-M4 (% RBCs) | ≥M6 (% RBCs) |
|---|---|---|---|---|
| [0; 2[ | 60.82 | 53.17 | 44.56 | 36.98 |
| [2; 4[ | 9.38 | 11.57 | 24.93 | 25.28 |
| [4; 6[ | 4.83 | 6.69 | 12.53 | 13.64 |
| [6; 8[ | 4.01 | 5.58 | 5.81 | 6.92 |
| [8; 10[ | 3.63 | 4.50 | 3.09 | 3.93 |
| [10; 15[ | 3.83 | 3.89 | 1.87 | 2.70 |
| [15; 20[ | 6.38 | 7.56 | 3.81 | 5.36 |
| ≥20 | 7.12 | 7.04 | 3.41 | 5.20 |

Tables 7 and 8: distribution of each red blood cell as a function of the content thereof of HbF categories (compared with total red blood cells) before and during the treatment with hydroxyurea.

The biological data of patients 11 and 24 were also analyzed (table 9 below).

TABLE 9

Biological data of patients 11 and 24. HbF = Hemoglobin F; RETIC = Reticulocytes; LDH = Lactate dehydrogenase; ASAT = Aspartate transaminase

| | Patient 11 (D 0) | Patient 11 (M 6) | Patient 24 (D 0) | Patient 24 (M 6) | Relative difference in % D 0 vs M 6 (patient 11) | Relative difference in % D 0 vs M 6 (patient 24) |
|---|---|---|---|---|---|---|
| HbF (g/dl) | 6.2 | 7.1 | 7.6 | 8.7 | +14.5 | +14.5 |
| RETIC (g/l) | 275 | 63 | 271 | 116 | −77.1 | −57.2 |
| LDH (IU/l) | 905 | 383 | 509 | 303 | −57.7 | −40.5 |
| ASAT (IU/l) | 55 | 26 | 32 | 29 | −52.7 | −9.4 |

The biological data showed that patients 11 and 24 exhibit identical relative differences in HbF (+14.5%) before and after six months of treatment with hydroxyurea. They nevertheless exhibit considerable differences in terms of HbF distribution (see table 8). Patient 11, compared with patient 24, exhibits, before treatment (D0), fewer RBCs having high protective HbF contents (17% RBCs vs 25% RBCs>6 pg of HbF), which might explain a greater anemia (6.2 g/dl vs 7.6 g/dl) and a greater hemolysis (LDH at 905 IU/l vs 509 IU/l). On the other hand, the increase in RBCs>6 pg HbF in patient 11 was more marked than in patient 24, at 6 months of treatment (57% vs 24%), and might explain a greater decrease in hemolysis under treatment (RETIC: −77% vs −57%; LDH: −57% vs −40.5%; ASAT −52% vs −9.4%).

Another example of distribution as a function of the HbF content of each red blood cell use represented for patient 2. Patient 2 exhibited, before the treatment with hydroxyurea, a relative homogeneity of HbF content distribution. However, at M6, the distribution was characterized by a clear increase in red blood cells containing a content greater than 20 pg to the detriment of all the other categories (table 10). It should be noted that the % HbF varies from 6% to 25% between D0 and M6, which is similar to the 2 previous examples.

TABLE 10 distribution of red blood cells as a function of the content thereof of HbF categories (compared with total red blood cells) before and during the treatment with hydroxyurea for patient 2

| HbF (pg) | D0 (% RBCs) | D15-M1 (% RBCs) | M3-M4 (% RBCs) | ≥M6 (% RBCs) |
|---|---|---|---|---|
| [0; 2[ | 22.43 | 9.21 | 5.29 | 4.98 |
| [2; 4[ | 15.76 | 14.72 | 8.62 | 7.04 |
| [4; 6[ | 12.85 | 9.52 | 10.61 | 5.53 |
| [6; 8[ | 10.04 | 8.47 | 10.39 | 4.85 |
| [8; 10[ | 7.84 | 7.35 | 8.75 | 4.56 |
| [10; 15[ | 5.79 | 9.03 | 8.50 | 7.48 |
| [15; 20[ | 11.05 | 14.27 | 14.54 | 9.75 |
| ≥20 | 14.24 | 27.43 | 33.30 | 55.81 |

6. Conclusion on the HbF Determination

The data showed that the red blood cells having a very low HbF content decreased greatly and that the red blood cells having an HbF content greater than 20 pg increase considerably, up to 3-fold, after 6 months of treatment with hydroxyurea.

7. Determination of the HbS Content (Pg) of Each RBC on the Basis of AG/RBC and the MCHbSCo The HbS/RBC was quantified in an unknown sample from SCD patients (not included in the linear regression, FIG. 7) using FACS assay and comparison of results between FACS and HPLC.

With the exception of the used anti-hemoglobin antibody (Anti HbS (mouse) Monoclonal Antibody 200 301 GS5, ROCKLAND® Number: 200 301 GS5.) Monoclonal Antibody), the same materials and methods were applied as described in the example "Determination of the HbF content (pg) of each RBC on the basis of AG/RBC and the MCHbFCo" above.

The FACS method allowed the HbS quantification in an unknown blood sample from a first subject (FIG. 8) and a second subject (FIG. 9) and the results were compared with a parallel HbS quantification with HPLC method. The results are presented in the following table 11.

| Subject 1: Mean HbS amount (HPLC): 18.5 | |
|---|---|
| HbS (pg) | RBC % |
| 0-5 | 0.1 |
| 5-10 | 1.0 |
| 10-15 | 6.0 |
| 15-20 | 13.9 |
| 20-25 | 18.1 |
| 25-30 | 18.1 |
| 30-35 | 15.7 |
| 35-40 | 12.3 |
| 40-45 | 8.7 |
| 45-50 | 6.1 |
| Subject 2: Mean HbS amount (HPLC): 29 | |
| HbS (pg) | RBC % |
| 0-5 | 0.0 |
| 5-10 | 1.4 |
| 10-15 | 4.7 |
| 15-20 | 8.8 |
| 20-25 | 13.7 |
| 25-30 | 17.4 |
| 30-35 | 17.0 |
| 35-40 | 15.0 |
| 40-45 | 12.2 |
| 45-50 | 9.8 |

Table 11 showing the results of the HbS determination according to the invention in subject 1 and subject 2.

As per in the case of the HbF determination, the present method allowed a detailed analysis of the HbS content in each cell of the blood sample.

7. Determination of the HbA Content (Pq) of Each RBC on the Basis of AG/RBC and the MCHbFCo The HbA/RBC was quantified in an unknown sample from two SCD patients (not included in the linear regression, FIG. 10) using FACS assay.

With the exception of the used anti-hemoglobin antibody (Anti HbA (mouse) Monoclonal Antibody 200 301 GS4, ROCKLAND® Number: 200 301 GS4), the same materials and methods were applied as described in the example "Determination of the HbF content (pg) of each RBC on the basis of AG/RBC and the MCHbFCo" above.

The invention claimed is:

1. A method for determining, in vitro, a content of at least one hemoglobin Hbx in each erythroid cell of a set of erythroid cells contained in a sample of erythroid cells, comprising the steps of:
   a) establishing a standard curve associating fluorescence intensity measured for erythroid cells with at least one hemoglobin Hbx content, using a homogeneous sample of erythroid cells:
   b) isolating erythroid cells from the sample;
   c) permeabilizing a membrane of the isolated erythroid cells;
   d) labeling the at least one hemoglobin Hbx of the erythroid cells obtained in step b) with at least one anti-Hbx antibody conjugated to a fluorochrome capable of emitting a fluorescence;
   e) measuring, by flow cytometry, fluorescence intensity (MFI) of each erythroid cell of the set of erythroid cells; and
   f) determining the content of the at least one hemoglobin Hbx in each erythroid cell of the set of erythroid cells by comparing the fluorescence intensity of each erythroid cell with the standard curve established in a), wherein establishing the standard curve comprises:
  establishing a calibration straight line which makes it possible to correlate a fluorescence intensity with a fluorophore number;
  obtaining a calibration blood sample from patients having an Hbx content that is homogeneous over all of their erythroid cells and having the Hbx labeled with an anti-Hbx antibody conjugated to a fluorophore;
  relating a measurement of fluorescence intensity in each erythroid cell in the calibration blood sample to the calibration straight line, such that it is possible to deduce an amount of fluorophore in each erythroid cell;
  deducing a number of Hbx molecules of each erythroid cell from the amount of fluorophore in each erythroid cell;
  determining a mean content of the at least one hemoglobin Hbx per erythroid cell (MCHbxCo) from the number of Hbx molecules of each erythroid cell; and
  establishing the standard curve by associating the MCHbxCo and a measurement of the fluorescence intensity in each erythroid cell in said calibration blood sample.

2. The method as claimed in claim 1, wherein the membrane of the isolated erythroid cells is fixed before the permeabilization step.

3. The method as claimed in claim 2, wherein the membrane of the isolated erythroid cells is fixed with sodium azide and/or formaldehyde.

4. The method as claimed in claim 1, wherein said sample is a blood sample.

5. The method as claimed in claim 4, wherein the blood sample is a human blood sample.

6. The method as claimed in claim 1, wherein said fluorochrome is selected from the group consisting of phycoerythrin (PE), fluorescein, isothiocyanate, a derivative thereof or a combination thereof.

7. The method as claimed in claim 1, wherein the at least one Hbx hemoglobin is at least one first hemoglobin Hbx1, at least one second hemoglobin Hbx2 and at least one $n^{th}$ hemoglobin designated as Hbxn, said method comprising the steps of:
  $b_1$) isolating erythroid cells from the sample;
  $c_1$) permeabilizing the membrane of the isolated erythroid cells;
  $d_1$) labeling the at least one first hemoglobin Hbx1 of the erythroid cells obtained in step $b_1$) with at least one anti-Hbx1 antibody conjugated to a first fluorochrome capable of emitting a first fluorescence; labeling the at least one second hemoglobin Hbx2 of the erythroid cells obtained in step $b_1$) with at least one second anti-Hbx2 antibody conjugated to a second fluorochrome capable of emitting a second fluorescence; labeling the at least one $n^{th}$ hemoglobin Hbxn of the erythroid cells obtained in step $b_1$) with at least one anti-Hbxn antibody conjugated to an $n^{th}$ fluorochrome capable of emitting a $n^{th}$ fluorescence,
  $e_1$) measuring, by flow cytometry, fluorescence intensity of each fluorescence emitted by the first, the second, and the $n^{th}$ fluorochrome of each erythroid cell of the set of erythroid cells;
  $f_1$) determining the content of the at least one first hemoglobin Hbx1, the at least one second hemoglobin Hbx2, and the at least one $n^{th}$ hemoglobin Hbxn in each erythroid cell of the set of erythroid cells by comparing each of the first, the second, the $n^{th}$ fluorescence intensities measured in step $e_1$) with a first, a second and an $n^{th}$ standard curve associating the measured first, second, and $n^{th}$ fluorescence intensities for an erythroid cell, with content of the at least one first hemoglobin Hbx1, content of the at least one second hemoglobin Hbx2 and content of the at least one $n^{th}$ hemoglobin Hbxn.

8. The method as claimed in claim 1, wherein the at least one Hbx hemoglobin are n hemoglobins Hbx, designated as Hbxn, said method comprising the steps of:
  $b_1$) isolating erythroid cells from the sample;
  $c_1$) permeabilizing the membrane of the isolated erythroid cells;
  $d_1$) labeling at least one first hemoglobin Hbx1 of the erythroid cells obtained in step $b_1$) with at least one anti-Hbx1 antibody conjugated to a fluorochrome;
  $e_1$) measuring, by flow cytometry, the fluorescence intensity (MFI) of each erythroid cell of the set of erythroid cells;
  $f_1$) determining the content of the at least one first hemoglobin Hbx1 in each erythroid cell of the set of erythroid cells by comparing the fluorescence intensity of each erythroid cell with a standard curve associating the fluorescence intensity measured for an erythroid cell labeled with at least one anti-Hbx1 antibody with the at least one first hemoglobin Hbx1 content; and
  $g_1$) iterating the steps $d_1$)-$f_1$) for each of at least one second Hbx2, at least one third Hbx3 and $n^{th}$ Hbxn hemoglobins until the content of the n hemoglobins Hbx in each erythroid cell of the set of erythroid cells is determined.

9. The method as claimed in claim 1, wherein said at least one anti-Hbx antibody is directed against at least one chain of the at least one hemoglobin Hbx that are selected from the group consisting of α, β, γ, δ, ε ζ chain, glycosylated derivatives thereof, blood disease variants thereof, mutated forms thereof, or a mixture thereof.

10. The method as claimed in claim 1, wherein said at least one hemoglobin Hbx is selected from the group consisting of HbF, HbA, HbS and a combination thereof.

11. The method as claimed in claim 1, wherein the membrane of the isolated erythroid cells is permeabilized with sodium dodecyl sulfate.

12. The method as claimed in claim 1, wherein the content of the at least one hemoglobin Hbx is determined for each erythroid cell of a set of at least 10,000 erythroid cells.

13. The method as claimed in claim 1, wherein the erythroid cells are red blood cells.

14. A method for determining, in vitro, an amount of erythroid cells transfused into a patient suffering from sickle cell disease, alpha-thalassemia or beta-thalassemia, comprising:
  a) determining a content of at least one hemoglobin Hbx selected from the group consisting of HbA, HbF and HbS of each erythroid cell of a set of erythroid cells of a sample of erythroid cells obtained from the patient according to the method of claim 13;
  b) using results of step a) to determine the amount of erythroid cells transfused into the patient, said transfused erythroid cells having an HbF and/or HbS content substantially equal to zero (=0 pg) and/or a content ratio of HbS/HbF+HbA) substantially equal to zero (=0).

15. An in vitro method for monitoring therapeutic efficacy of a Hematopoietic stem cell transplantation (HSCT) or of a treatment for myelodysplastic syndromes, sickle cell disease or for B-thalassemia, comprising:

a) obtaining a sample containing erythroid cells from a patient having undergone a HSCT or a treatment for a myelodysplastic syndrome, sickle cell disease or for B-thalassemia;
b) determining a content of at least one hemoglobin Hbx in each erythroid cell of a set of erythroid cells of said sample according to the method of claim 13;
c) using results of step b) in the monitoring of the therapeutic efficacy of Hematopoietic stem cell transplantation (HSCT) or the treatment for myelodysplastic syndromes, sickle cell disease or for B-thalassemia, in which a therapeutic efficacy is observed when at least a predetermined percentage of the erythroid cells of the set of erythroid cells has a content of the at least one hemoglobin Hbx that increases or decreases at least 2%, at least 5%, at least 7%, at least 10%, at least 12%, at least 15%, or at least 20% compared to a same content prior to the HSCT or the treatment for myelodysplastic syndromes, sickle cell disease or for B-thalassemia.

16. A method for treating myelodysplastic syndromes, sickle cell disease or B-thalassemia, comprising:
a) obtaining a sample containing erythroid cells from a patient having myelodysplastic syndromes, sickle cell disease or B-thalassemia;
b) determining at least one hemoglobin Hbx content selected from the group consisting of HbF, HbA and HbS content of each erythroid cell of a set of erythroid cells of said sample according to the method of claim 13;
c) when at least a predetermined percentage of the erythroid cells of the set of erythroid cells has an HbS content which exceeds a HbS reference threshold, and/or when at least a predetermined percentage of the erythroid cells of the set of erythroid cells has an HbF and/or HbA content below a HbF and/or HbA reference threshold, initiating a treatment in the patient with myelodysplastic syndromes, sickle cell disease or B-thalassemia.

17. The method as claimed in claim 16, wherein at least 20% of the erythroid cells of the set of erythroid cells have an HbF content which is below the reference threshold.

18. The method as claimed in claim 17, wherein the reference threshold is selected from the group consisting of 2 pg, 3 pg, 4 pg, 5 pg, 6 pg, 7 pg, and 7.5 pg.

19. The method as claimed in claim 16, wherein the treatment is hydroxyurea and/or erythropoietin.

20. The method as claimed in claim 1, wherein the content of the at least one hemoglobin Hbx in each erythroid cell of the set of erythroid cells is expressed as a concentration relative to a volume of the erythroid cells.

* * * * *